United States Patent
Larsson et al.

(10) Patent No.: US 7,037,925 B2
(45) Date of Patent: May 2, 2006

(54) 4-ANILINOQUINOLINE-3-CARBOXAMIDES

(75) Inventors: Joakim Larsson, Lund (SE); Peter Sjö, Lund (SE)

(73) Assignee: AstraZeneca AB, Sodertalje (SE)

( * ) Notice: Subject to any disclaimer, the term of this patent is extended or adjusted under 35 U.S.C. 154(b) by 107 days.

(21) Appl. No.: 10/477,254

(22) PCT Filed: May 6, 2002

(86) PCT No.: PCT/SE02/00875

§ 371 (c)(1),
(2), (4) Date: Nov. 10, 2003

(87) PCT Pub. No.: WO02/092571

PCT Pub. Date: Nov. 21, 2002

(65) Prior Publication Data

US 2004/0248923 A1    Dec. 9, 2004

(30) Foreign Application Priority Data

May 11, 2001  (SE) .................................. 0101675

(51) Int. Cl.
*A61K 31/47* (2006.01)
*C07D 215/38* (2006.01)
(52) U.S. Cl. ...................... 514/312; 546/159
(58) Field of Classification Search ............... 546/159; 514/312
See application file for complete search history.

(56) References Cited

FOREIGN PATENT DOCUMENTS

| WO | WO 9843960 A1 | 8/1998 |
|---|---|---|
| WO | WO 98/43960 | * 10/1998 |
| WO | WO 0010981 A1 | 2/2000 |

OTHER PUBLICATIONS

Sen, Chemical Abstracts 34:75700, 1965.*
Boschelli, J Med Chem, vol. 44, pp 822-833, 2001.*
Vissner, J Med Chem, VOI 43, pp 3244-3256, 2000.*
J. Med. Chew., vol. 44, No. 5, Mar. 2001, Diane H. Boschelli et al: "Synthesis and Src Kinase Inhibitory Activity of a Series of 4-Phenylamino-3-quinolinecarbonitriles", pp.822-833, p. 823, No. 19.
J. Med. Chem., vol. 43, No. 17, 2000, Allan Wissner et al: "4-Anilino-6,7-ialkoxyquinoline-3-carbonitrile Inhibitors of Epidermal Growth Factor Receptor Kinase and Their Bioisosteric Relationship to the 4-Anilino-6,7-dialkoxyquinazoline Inhibitors", p. 3244 - p. 3256; p. 3249, No. 54; p. 3255, p.3248.
STN Internal, File Ca, CAOLD, accession No. CA64: 14164b, Sen, Achintya K. et al: "Synthesis of 4-aminoquinolines"; J. Indian Chem. Soc. 42(12), 851-4 (1965)(Eng)., RN 5382-40-1.

* cited by examiner

*Primary Examiner*—D. Margaret Seaman

(57) ABSTRACT

The present invention relates to novel compounds of formula (IA), which are JAK3 Kinase inhibitors, methods for their preparation and pharmaceutical compositions comprising them.

7 Claims, No Drawings

4-ANILINOQUINOLINE-3-CARBOXAMIDES

CROSS-REFERENCE TO RELATED APPLICATIONS

This application is the national phase application under 35 U.S.C. § 371 of PCT International Application No. PCT/SE02/00875 which has an International filing date of May 6, 2002, which designated the May 11, 2001, the contents of which is incorporated by reference in its entirety.

The present invention relates to novel compounds which are JAK3 Kinase inhibitors, methods for their preparation, intermediates and pharmaceutical compositions comprising them.

Janus Kinase 3 (JAK3) is a member of the Janus family of protein kinases. Although the other members of this family are expressed by essentially all tissues, JAK3 expression is limited to hematopoetic cells. This is consistent with its essential role in signaling through the receptors for IL-2, IL-4, IL-7, IL-9, IL-13 and IL-15 by non-covalent association of JAK3 with the gamma chain common to these multichain receptors. These cytokines all have a shared function in that they are involved in lymphocyte differentiation and proliferation. XSCID patient populations have been identified with severely reduced levels of JAK3 protein or with genetic defects to the common gamma chain, suggesting that immunosuppression should result from blocking signaling through the JAK3 pathway. Animal studies have suggested that JAK3 not only play a critical role in B- and T-lymphocyte maturation, but that JAK3 is constitutively required to maintain T-cell function. Modulation of immune activity through this novel mechanism can prove useful in the treatment of T-cell proliferative disorders such as transplant rejection and autoimmune diseases.

The role of JAK3 in mast cells has been described in knockout mice. Thus, IgE/antigen induced degranulation and mediator releases were substantially reduced in mast cells generated from JAK3 deficient mice. JAK3 deficiency does not affect mast cell proliferation in vitro, it has also been shown that IgE receptor levels and mediator contents are identical in JAK3−/− and JAK3 +/+ mast cells. Therefore, JAK3 appears essential for the complete response of IgE challenged mast cells. The role of JAK3 in mast cell activation has been well established in murine system, however, there is no published data on mast cell function in the AR-SCID patients. Targeting JAK3 provides the basis for new and effective treatment of mast cell mediated allergic reactions.

To date a number of JAK3 inhibitors has been disclosed, among them are quinazolines (Sudbeck, E. A. et al. Clinical Cancer Res. 5(1999)1569–82, WO 00/0202) and pyrrol[2,3-d]pyrimidines (Blumenkopf, T. A. et al. WO 99/65909).

In the current application compounds, 4-anilinoquinoline-3-carboxamides, are claimed as JAK3 inhibitors. Structurally related compounds have previously been described as kinase inhibitors e.g. WO 00/18761 and WO 98/43960 disclose substituted quinoline-3-carbonitrile derivatives. In a recent publication (Boschelli, D. H. et al. J. Med. Chem. 44(2001)822–33) one compound of the present invention has proved not to have any inhibitory capacity towards the activity of the protein tyrosine kinase Src. JAK3 is not mentioned in any of the above literature examples.

Two compounds and their synthesis relating to this invention have previously been described (Boschelli, D. H. et al. J. Med. Chem. 44(2001)822–33 and Wissner et al. WO 98/43960).

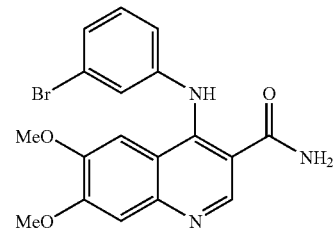

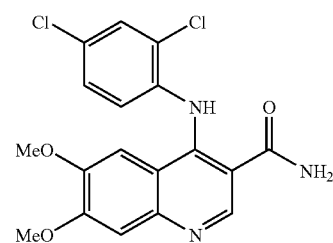

The present invention therefore provides a compound of formula (I) for use in the manufacture of a medicament for the treatment of a disease mediated by JAK3:

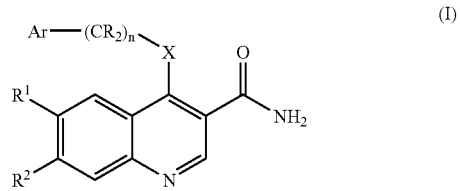

(I)

wherein:
n is 0 or 1;
X is $NR^3$ or O;
Ar is selected from phenyl, tetrahydronaphthenyl, indolyl, pyrazolyl, dihydroindenyl, 1-oxo-2,3-dihydroindenyl or indazolyl, each of which can be optionally substituted by one or more groups selected from halogen, hydroxy, cyano, $C_1$–$C_8$ alkoxy, $CO_2R^8$, $CONR^9R^{10}$, $C_1$–$C_8$ alkyl-O—$C_1$–$C_8$ alkyl, $C_1$–$C_8$ alkyl-$NR^8$—$C_1$–$C_8$ alkyl, $C_1$–$C_8$ alkyl-$CONR^8$—$C_1$–$C_8$ alkyl, $C_1$–$C_8$ alkyl-$CONR^9R^{10}$, $NR^8COC_1$–$C_8$ alkyl, $C_1$–$C_8$ thioalkyl, $C_1$–$C_8$ alkyl (itself optionally substituted by one or more hydroxy or cyano groups or fluorine atoms) or $C_1$–$C_8$ alkoxy;
R groups are independently hydrogen or $C_1$–$C_8$ alkyl;
$R^1$ and $R^2$ are independently selected from hydrogen, halogen, nitro, cyano, $C_1$–$C_8$ alkyl, $C_1$–$C_8$ alkoxy, hydroxy, aryl, $Y(CR^{11}_2)_pNR^4R^5$, $Y(CR^{11}_2)_pCONR^4R^5$, $Y(CR^{11}_2)_pCO_2R^6$, $Y(CR^{11}_2)_pOR^6$; $Y(CR^{11}_2)_pR^6$;
or $R^1$ and $R^2$ are linked together as —$OCH_2O$— or —$OCH_2CH_2O$—;
$R^{11}$ groups are independently hydrogen, $C_1$–$C_8$ alkyl, hydroxy or halogen;
p is 0, 1, 2, 3, 4 or 5;
Y is oxygen, $CH_2$ or $NR^7$
$R^3$ is hydrogen or $C_1$–$C_8$ alkyl;
$R^4$ and $R^5$ each independently represent hydrogen, $C_1$–$C_8$ alkyl or $R^4$ and $R^5$ together with the nitrogen atom to which they are attached form a 4- to 7-membered saturated or aromatic heterocyclic ring system optionally containing a further oxygen, sulphur or $NR^6$ group, or one of $R^4$ and $R^5$ is hydrogen or $C_1$–$C_8$ alkyl and the other is a 5- or 6-membered heterocyclic ring system optionally containing a further oxygen, sulphur or nitrogen atom;

$R^6$ is hydrogen, $C_1$–$C_8$ alkyl, phenyl or benzyl;

$R^7$ is hydrogen or $C_1$–$C_8$ alkyl;

$R^8$ is hydrogen or $C_1$–$C_8$ alkyl;

$R^9$ and $R^{10}$ are each independently hydrogen or $C_1$–$C_8$ alkyl and pharmaceutically acceptable salts thereof.

The term alkyl, whether used alone or as part of another group such as alkoxy, means any straight or branched chained alkyl group. The term aryl includes phenyl and naphthyl groups.

Suitably the R groups are independently hydrogen or $C_1$–$C_8$ alkyl, preferably hydrogen or methyl, and most preferably both R groups are hydrogen.

Suitably X is $NR^3$ or O. Preferably X is $NR^3$ where $R^3$ is $C_{1-4}$alkyl, more preferably X is NH.

Suitably n is 0 or 1, preferably n is 0.

Suitably p is 0, 1, 2, 3, 4 or 5, preferably p is 1 to 4, more preferably p is 2 or 3.

Suitably Ar is selected from phenyl, tetrahydronaphthenyl, indolyl, pyrazolyl, dihydroindenyl, 1-oxo-2,3-dihydroindenyl or indazolyl optionally substituted as described above. Substituents can be present on any suitable position of the Ar group. More than one substituent can be present, and these can be the same or different. Preferably Ar is indolyl or phenyl, most preferably phenyl.

More preferably the Ar group is unsubstituted or has one or more substituents including those of compounds exemplified herein such as methyl, ethyl, propyl, butyl, thiomethyl, hydroxymethyl, bromo, fluoro, hydroxy, $CO_2H$, $CONH_2$, $CF_3$, methoxymethyl, butoxymethyl, cyanomethyl, ethylaminomethyl, aminomethyl, ethylamino-2-oxoethyl, hydroxyethyl, 2-amino-2-oxoethyl, $CO_2CH_3$, methoxy or ethoxy. When Ar is phenyl then one or two substituent groups are preferred. Even more preferred substituents include ethyl, n-propyl, iso-propyl, hydroxymethyl, hydroxyethyl, thiomethyl, aminomethyl, bromo and $CO_2H$. Most preferrred substituents are methyl, ethyl and hydroxymethyl.

Suitably $R^1$ and $R^2$ are independently selected from hydrogen, halogen, nitro, cyano, $C_1$–$C_8$ alkyl, $C_1$–$C_8$ alkoxy, hydroxy, $Y(CH_2)_pNR^4R^5$, $Y(CH_2)_pCONR^4R^5$, $Y(CH_2)_pCO_2R^6$, $Y(CH_2)_pOR^6$; $Y(CH_2)_pR^6$; or $R^1$ or $R^2$ are linked together as —$OCH_2O$— or —$OCH_2CH_2O$—. Preferably $R^1$ and $R^2$ are hydrogen chloro, methoxy, ethoxy, $O(CH_2)_2NR^4R^5$, $O(CH_2)_3NR^4R^5$, $NH(CH_2)_2NR^4R^5$ or $NH(CH^2)_2)NR^4R^5$ where $R^4$ and $R^5$ are hydrogen or methyl or one is methyl and the other is pyridyl or $R^4$ and $R^5$ form a morpholine, 3,5-dimethylmorpholine, thiomorpholine, pyrrolidine, pyrrolidine, piperazine (optionally substituted), piperidine, triazole or imidazolyl ring, or $R^4$ and $R^5$ are independently $O(CH_2)_3CO_2CH_3$, O-benzyl, 1-benyzl-4-pieridinylamino, $O(CH_2)_2NMe_2$, $OCH_2CONH_2$, $O(CH_2)_2NHMe$, $O(CH_2)_3NH_2$, nitro or cyano; or $R^1$ and $R^2$ are linked together as —$OCH_2O$— or —$OCH_2CH_2O$—

Where $R^4$ and $R^5$ form a 4- to 7-membered saturated or aromatic heterocyclic ring system suitable examples of such rings include morpholine, 3,5-dimethylmorpholine, 2,6-dimethylmorpholine, thiomorpholine, pyrrolidine, piperazine (optionally substituted by $C_1$–$C_8$ alkyl, piperidine, triazole or imidazolyl.

Where one of $R^4$ and $R^5$ is hydrogen or $C_1$–$C_8$ alkyl and the other is a 5- or 6-membered heterocyclic ring system optionally containing a further oxygen, sulphur or nitrogen atom; examples of such rings include thienyl, furyl, pyrimidyl, imidazolyl, pyridyl and pyrazole.

Most preferably $R^1$ is methoxy, ethoxy, $OCH_2CONH_2$, $O(CH_2)_2OMe$, $O(CH_2)_3OH$, $O(CH_2)_3CO_2Me$, $O(CH_2)_2NR^4R^5$, $O(CH_2)_3NR^4R^5$, $O(CH_2)_4NR^4R^5$ where $R^4$ and $R^5$ are both hydrogen or methyl or together with the nitrogen to which they are attached form a piperidine or morpholine ring, or $R^1$ is $NH(CH_2)_3NR^4R^5$ where $R^4$ and $R^5$ together with the nitrogen to which they are attached form an imidazole ring.

Most preferably $R^2$ is methoxy, ethoxy, $OCH_2CONH_2$, $O(CH_2)_2OMe$, $O(CH_2)_3OH$, $O(CH_2)_3CO_2Me$, $O(CH_2)_2NR^4R^5$, $O(CH_2)_3NR^4R^5$ or $O(CH_2)_4NR^4R^5$ where one of $R^4$ or $R^5$ is methyl and the other is pyridyl, or $R^4$ and $R^5$ are selected from hydrogen or methyl or together with the nitrogen to which they are attached form a thiomorpholine, piperidine, morpholine, imidazole, triazole or 2,6-dimethylmorpholine group.

Most preferred compounds are those wherein $R^1$ and/or $R^2$ are both methoxy or ethoxy, or one is methoxy and the other is ethoxy.

Especially preferred compounds of the invention include those exemplified herein, both in free base form and as pharmaceutically acceptable salts.

Compounds of the invention can form pharmaceutically acceptable solvates and salts. The compounds of the formula (I) can form acid addition salts with acids, such as conventional pharmaceutically acceptable acids, for example maleic, hydrochloric, hydrobromic, phosphoric, acetic, fumaric, salicyclic, citric, lactic, mandelic, tartaric, trifluoroacetic and methanesulphonic acids.

The invention also provides a method of treating or preventing a disease mediated by JAK3 which comprises administering to a mammal a compound of formula (I) as defined above.

In a further aspect the invention provides a compound of formula (I) as defined above but excluding the compounds 4-(2-bromoanilino)-6,7-dimethoxy-3-quinolinecarboxamide and 4-(1,5-dichloroanilino)-6,7-dimethoxy-3-quinolinecarboxamide for use in therapy, Certain compounds of formula (I) are believed to be novel and therefore all novel compounds form a further aspect of the invention. The invention therefore provides a compound of formula (IA):

(IA)

in which

Ar is phenyl substituted by ethyl, propyl, hydroxymethyl or $CO_2H$ or disubstituted by methyl and hydroxymethyl;

$R^1$ is methoxy, ethoxy or a group $OCH_2CONH_2$, $OCH_2CH_2OCH_3$, or $O(CH_2)_pNR^4R^5$ where p is 2 or 3 and $R^4$ and $R^5$ are hydrogen, methyl, ethyl or propyl or together $R^4$ and $R^5$ form a pyrrolidine, imidazole or morpholine ring;

$R^2$ is methoxy, ethoxy or $O(CH_2)_pNR^4R^5$ where p is 2, 3 or 4 and $R^4$ and $R^5$ are hydrogen, methyl or ethyl or one of $R^4$ or $R^5$ is methyl and the other is pyridyl or pyrazole or $R^4$ and $R^5$ form a piperidine, hydroxypiperidine, thiomorpholine, morpholine, pyrrolidine, 2,6-dimethylmorpholine imidazole or triazole ring, or a pharmaceutically acceptable salt or solvate thereof, provided that when A is phenyl substituted by ethyl or propyl or disubstituted by methyl, then $R^1$ and $R^2$ are not both methoxy, $R^1$ and $R^2$ are not both ethoxy or one of $R^1/R^2$ is not methoxy when the other is ethoxy.

Preferred compounds of formula (IA) are those novel compounds exemplified herein:

4-(2-ethylanilino)-6-methoxy-7-{2-[methyl(4-pyridinyl) amino]ethoxy}-3-quinolinecarboxamide,
4-[3-(hydroxymethyl)-2-methylanilino]-6-methoxy-7-[3-(4-thiomorpholinyl)propoxy]-3-quinolinecarboxamide,
4-[3-(hydroxymethyl)-2-methylanilino]-6-methoxy-7-[3-(1-piperidinyl)propoxy]-3-quinolinecarboxamide,
4-[3-(hydroxymethyl)-2-methylanilino]-6-methoxy-7-[3-(4-morpholinyl)propoxy]-3-quinolinecarboxamide,
7-[3-(dimethylamino)propoxy]-4-(2-ethylanilino)-6-methoxy-3-quinolinecarboxamide,
7-[3-(dimethylamino)propoxy]-4-[3-(hydroxymethyl)-2-methylanilino]-6-methoxy-3-quinolinecarboxamide,
7-{3-[(2R,6S)-2,6-dimethylmorpholinyl]propoxy}-4-[3-(hydroxymethyl)-2-methylanilino]-6-methoxy-3-quinolinecarboxamide,
4-(2-ethylanilino)-6-methoxy-7-[3-(4-morpholinyl)propoxy]-3-quinolinecarboxamide,
4-(2-ethylanilino)-6-methoxy-7-[4-(4-morpholinyl)butoxy]-3-quinolinecarboxamide,
4-(2-ethylanilino)-6-methoxy-7-{3-[methyl(4-pyridinyl) propoxy}-3-quinolinecarboxamide,
4-(2-ethylanilino)-7-methoxy-6-[2-(methylamino)ethoxy]-3-quinolinecarboxamide,
7-{3-[(2S,6S)-2,6-dimethylmorpholinyl]propoxy}-4-[3-(hydroxymethyl)-2-methylanilino]-6-methoxy-3-quinolinecarboxamide,
4-(2-ethylanilino)-7-[3-(1H-imidazol-1-yl)propoxy]-6-methoxy-3-quinolinecarboxamide,
6-(2-aminoethoxy)-4-(2-ethylanilino)-7-methoxy-3-quinolinecarboxamide,
6-methoxy-4-[2-(methylsulfanyl)anilino]-7-[3-(4-morpholinyl)propoxy]-3-quinolinecarboxamide,
6-methoxy-7-[3-(4-morpholinyl)propoxy]-4-(2-toluidino)-3-quinolinecarboxamide,
4-(2-ethylanilino)-6-methoxy-7-[3-(1H-1,2,4-triazol-1-yl) propoxy]-3-quinolinecarboxamide,
4-(2-ethylanilino)-6-methoxy-7-[2-(methylamino)ethoxy]-3-quinolinecarboxamide,
4-(2-ethylanilino)-6-methoxy-7-(2-methoxyethoxy)-3-quinolinecarboxamide,
4-(2-ethylanilino)-7-(3-hydroxypropoxy-6-methoxy-3-quinolinecarboxamide,
6-methoxy-7-[2-(4-morpholinyl)ethoxy]-4-(2-toluidino)-3-quinolinecarboxamide,
4-[3-(hydroxymethyl)-2-methylanilino]-7-methoxy-6-[2-(1-pyrrolidinyl)ethoxy]-3-quinolinecarboxamide
3-{[3-(aminocarbonyl)-6,7-dimethoxy-4-quinolinyl] amino}-2-methylbenzoic acid,
4-[3-(hydroxymethyl)-2-methylanilino]-6,7-dimethoxy-3-quinolinecarboxamide,
4-(2-ethylanilino)-7-[2-(1H-imidazol-1-yl)ethoxy]-6-methoxy-3-quinolinecarboxamide,
4-(2-hydroxyethyl)-2-methylanilino]-6,7-dimethoxy-3-quinolinecarboxamide,
7-methoxy-6-{[2-(4-morpholinyl)ethyl]amino}-4-(2-toluidino)-3-quinolinecarboxamide,
4-(2-ethylanilino)-6-[3-(1H-imidazol-1-yl)propoxy]-7-methoxy-3-quinolinecarboxamide,
4-(2-ethylanilino)-7-methoxy-6-[2-(1-pyrrolidinyl)ethoxy]-3-quinolinecarboxamide,
7-(3-aminopropoxy)-4-(2-ethylanilino)-6-methoxy-3-quinolinecarboxamide,
methyl 4-{[3-(aminocarbonyl)-6-methoxy-4-(2-toluidino)-7-quinolinyl]oxy}butanoate,
4-[3-(aminomethyl)-2-methylanilino]-6,7-dimethoxy-3-quinolinecarboxamide,
6-{[3-(1H-imidazol-1-yl)propyl]amino}-7-methoxy-4-(2-toluidino)-3-quinolinecarboxamide,
4-[3-(hydroxymethyl)-2-methylanilino]-7-methoxy-6-(2-methoxyethoxy)-3-quinolinecarboxamide,
6-[2-(dimethylamino)ethoxy]-4-(2-ethylanilino)-7-methoxy-3-quinolinecarboxamide,
4-[3-(cyanomethyl)-2-methylanilino]-6,7-dimethoxy-3-quinolinecarboxamide,
4-[3-(2-amino-2-oxoethyl)-2-methylanilino]-6,7-dimethoxy-3-quinolinecarboxamide,
6-(3-aminopropoxy)-4-(2-ethylanilino)-7-methoxy-3-quinolinecarboxamide,
4-[3-(hydroxymethyl)-2-methylanilino]-7-methoxy-6-[3-(4-morpholinyl)propoxy]-3-quinolinecarboxamide,
4-[3-(hydroxymethyl)-2-methylanilino]-7-methoxy-6-[2-(4-morpholinyl)ethoxy]-3-quinolinecarboxamide, and pharmaceutically acceptable salts thereof.

Further novel compounds of formula (IA) include those of examples 186–217.

Compounds of the present invention include all stereoisomers, pure and mixed racemates, and mixtures thereof. Tautomers of compounds of formula (I) and (IA) also form an aspect of the invention.

In a further aspect the invention provides a process for the preparation of a compound of formula (I) which comprises:

(a) reaction of a compound of formula (II):

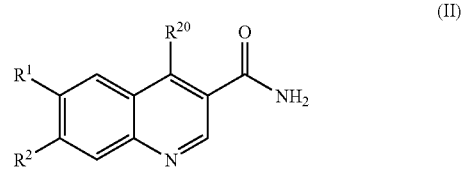

in which $R^1$ and $R^2$ are as defined in formula (I) or are protected derivatives thereof and $R^{20}$ is a leaving group, with a compound of formula (III):

in which Ar and R are as defined in formula (I) or are protected derivatives thereof, or (b) for compounds of formula (I) where $R^1$ and/or $R^2$ are groups $Y(CH_2)_pNR^4R^5$, $Y(CH_2)_pCONR^4R^5$, $Y(CH_2)_pCO_2R^6$, $Y(CH_2)_pOR^6$ or $Y(CH_2)_pR^6$ where Y is oxygen, reaction of a compound of formula (IV):

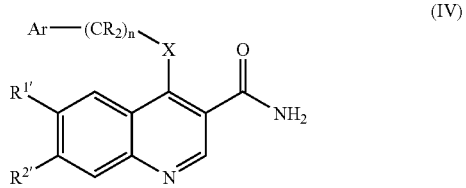

(IV)

where the $R^{1'}$ or $R^{2'}$ to be converted into a group $Y(CH_2)_pNR^4R^5$, $Y(CH_2)_pCO_2R^6$, $Y(CH_2)_pOR^6$ or $Y(CH^2)_pR^6$ is hydroxy and the other $R^{1'}$ or $R^{2'}$ together with Ar are as defined above for process (a) with a compound of formula (V):

(V)

where $R^{21}$ is $NR^4R^5$, $CONR^4R^5$, $CO_2R^6$, $OR^6$ or $R^6$ and $R^4$, $R^5$ and $R^6$ are as defined in formula (I) or are protected derivatives thereof, and optionally thereafter process (a) or (b)

removing any protecting groups converting a compound of formula (I) into a further compound of formula (I)

forming a pharmaceutically acceptable salt.

In process (a) the group $R^{20}$ is a leaving group such as halogen, in particular chloro. The reaction can be carried out in an inert solvent such as DMF at elevated temperature, for example at about 100° C.

In process (b) the leaving group L is preferably halogen, in particular chloro. The reaction can be carried out in the presence of a base such as cesium carbonate in an inert solvent such as DMF or ethanol.

Compounds of formula (II) can be prepared by reacting compounds of formula (VI):

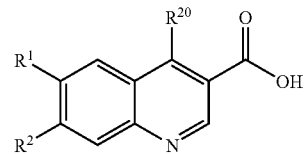

(VI)

in which $R^1$, $R^2$ and $R^{20}$ are as defined in formula (II) with a chlorinating agent such as thionyl chloride, and reaction of the corresponding acid chloride with ammonia.

Compounds of formula (VI) can be prepared using literature chemistry.

It will be appreciated that certain functional groups may need to be protected using standard protecting groups. The protection and deprotection of functional groups is for example, described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Diseases mediated by JAK3 include inflammatory, immunological, and bronchopulmonary disorders.

The present invention also relates to a pharmaceutical composition for (a) treating or preventing a disorder or condition selected from organ transplant rejection, lupus, multiple sclerosis, rheumatoid arthritis, psoriasis, Type I diabetes and complications from diabetes, cancer, asthma, rhinitis, atopic dermatitis, autoimmune thyroid disorders, ulcerative colitis, Crohn's disease, Alzheimer's disease, leukemia, and other autoimmune diseases or (b) the inhibition of protein tyrosine kinases or Janus kinase 3 (JAK3) in a mammal, including a human, comprising an amount of a compound of formula I or a pharmaceutically acceptable salt thereof, effective in such disorders or conditions and a pharmaceutically acceptable carrier.

Preferably the compounds of the invention are useful for the treatment of asthma, rheumatoid arthritis, and host versus graft rejection/transplantation.

The present invention also relates to a pharmaceutical composition for (a) treating or preventing a disorder or condition selected from organ transplant rejection, lupus, multiple sclerosis, rheumatoid arthritis, psoriasis, Type I diabetes and complications from diabetes, cane, asthma, rhinitis, atopic dermatitis, autoimmune thyroid disorders, ulcerative colitis, Crohn's disease, Alzheimer's disease, leukemia, and other autoimmune diseases or (b) the inhibition of protein tyrosine kinases or Janus kinase 3 (JAK3) in a mammal, including a human, comprising an amount of a compound of formula I or a pharmaceutically acceptable salt thereof, alone or in combination with a T-cell immunosuppresant or anti-inflammatory agents, effective in such disorders or conditions and a pharmaceutically acceptable carrier.

The present invention also relates to a method for the inhibition of protein tyrosine kinases or Janus Kinase 3 (JAK3) in a mammal, including human, comprising administering to said mammal an effective amount of a compound of formula I or a pharmaceutically acceptable salt thereof.

In a still further aspect the invention provides the use of a compound of formula (IA) as a therapeutic agent.

The dose of the compound to be administered will depend on the relevant indication, the age, weight and sex of the patient and may be determined by a physician. The dosage will preferably be in the range of from 0.1 mg/kg to 100 mg/kg.

The compounds may be administered topically, e.g. to the lung and/or the airways, in the form of solutions, suspensions, HFA aerosols or dry powder formulations, e.g. formulations in the inhaler device known as the Turbuhaler®; or systemically, e.g. by oral administration in the form of tablets, pills, capsules, syrups, powders or granules, or by parenteral administration, e.g. in the form of sterile parenteral solutions or suspensions, or by rectal administration, e.g. in the form of suppositories.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurized HFA aerosols of the compounds of the invention may be administered by oral or nasal inhalation. For inhalation the compound is desirably finely divided. The finely divided compound preferably has a mass median diameter of less than 10 μm, and may be suspended in a propellant mixture with the assistance of a dispersant, such as a $C_8$–$C_{20}$ fatty acid or salt thereof, (e.g. oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol, or an other polyol. Suitable carriers are sugars, e.g. lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound, with or without a carrier substance, is delivered to the patient.

For oral administration the active compound may be admixed with an adjuvant or a carrier, e.g. lactose, saccharose, sorbitol, mannitol; a starch, e.g. potato starch, corn starch or amylopectin; a cellulose derivative; a binder, e.g. gelatine or polyvinylpyrrolidone, and/or a lubricant, e.g. magnesium stearate, calcium stearate, polyethylene glycol, a wax, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved in a readily volatile organic solvent.

For the preparation of soft gelatine capsules, the compound may be admixed with e.g. a vegetable oil or polyethylene glycol. Hard gelatine capsules may contain granules of the compound using either the above mentioned excipients for tablets. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

The term 'medical therapy' as used herein is intended to include prophylactic, diagnostic and therapeutic regimens carried out in vivo or ex vivo on humans or other mammals.

The following Examples illustrate the invention.

General methods All reactions were performed in dried glassware in an argon atmosphere at room temperature, unless otherwise noted. All solvents and reagents and solvents were used as received. Merck Silica gel 60 (0.040–0.063 mm) was used for preparative silica gel chromatography. A Kromasil KR-100-5-C18 column (250×20 mm, Akzo Nobel) and mixtures of acetonitrile/water at a flow rate of 10 ml/min was used for preparative HPLC. Reactions were monitored at 254 nm by analytical HPLC, using a Kromasil C-18 column (150×4.6 mm) and a gradient (containing 0.1% trifluoroacetic acid) of 5 to 100% of acetonitrile in water at a flow rate of 1 ml/min. Evaporations of solvents were performed under reduced pressure using a rotary evaporator at a maximum temperature of 40° C. Products were dried under reduced pressure at 40° C.

$^1$H-NMR spectra were recorded on a Varian Inova-400 or Unity-500+ instrument. The central solvent peak of chloroform-d ($\delta_H$ 7.27 ppm), dimethylsulfoxide-d$_6$ ($\delta_H$ 2.50 ppm) or methanol-d$_4$ ($\delta_H$ 3.35 ppm) were used as internal references. Low resolution mass spectra obtained on a Hewlett Packard 1100 LC-MS system equipped with a APCI ionisation chamber.

Merck Silica gel 60 (0.040–0.063 mm) was used for preparative silica gel chromatography. A Kromasil KR-100-5-C18 column (250×20 mm, Akzo Nobel) and mixtures of acetonitrile/water at a flow rate of 10 ml/min was used for preparative HPLC. Reactions were monitored at 254 nm by analytical HPLC, using a Kromasil C-18 column (150×4.6 mm) and a gradient (containing 0.1% trifluoroacetic acid) of 5 to 100% of acetonitrile in water at a flow rate of 1 ml/min. Evaporations of solvents were performed under reduced pressure using a rotary evaporator at a maximum temperature of 40° C. Products were dried under reduced pressure at 40° C.

EXAMPLE 1

6-(Benzyloxy)-4-[3-(hydroxymethyl)-2-methylanilino]-7-methoxy-3-quinolinecarboxamide a) 1-(Benzyloxy)-2-methoxy-4-nitrobenzene 4-Nitroguaiacol potassium salt monohydrate (25 g, 111 mmol) and cesium carbonate (3.25 g, 10 mmol) were transferred into a 500 ml one-neck flask and dry dimethylformamide (200 ml) was added, benzyl bromide (21.4 g, 125 mmol) was added dropwise at room temperature under N$_2$ atmosphere and the reaction mixture was stirred vigorously for about 3 hours. The solvent and the excess of benzylbromide were then removed under reduced pressure. Water (200 ml) and ethanol (100 ml) was added to the crude product and refluxed for 10–15 minutes. The yellowish crystals were filtered from the cold mixture, washed with water and dried to give 29 g (100% yield) of the title compound.

$^1$H NMR (CDCl$_3$): δ 7.85 (1H, dd); 7.77 (1H, d); 7.46–7.32 (5H, m); 5.26 (2H, s); 3.97 (3H, s).

b) 4-(Benzyloxy)-3-methoxyaniline.

To 1-(Benzyloxy)-2-methoxy-4-nitrobenzene (26 g, 100 mmol) dissolved in ethanol (500 ml) in a 2 liter one-neck flask was added dropwise under 30 minutes a solution af sodium dithionite in water (500 ml), stirring was continued at ambient temperature for 2 h and after that the reaction mixture was heated at 70–80° C. for approx. 4 h, cooled and alkalized with sodium carbonate. The precipitate was filtered, washed with water and dried. The combined water phases were extracted with ethylacetate. The combined organic phases were washed with water, dried over sodium sulfate, filtered and evaporated to dryness. The residue was combined with the filtered precipitate to afford 9.3 g (41% yield) of the product.

$^1$H NMR (DMSO-d$_6$): δ 7.42–7.24 (5H, m); 6.67 (1H, d); 6.27 (1H, d); 6.02 (1H, dd); 4.86 (2H, s); 4.68 (2H, s); 3.67 (3H, s).

c) Diethyl 2-(4-benzyloxy-3-methoxyanilino)methylenemalonate

A mixture of 4-(Benzyloxy)-3-methoxyaniline (9.3 g, 40 mmol) and diethyl ethoxymethylenemalonate (9.65 g, 45 mmol) were heated at 120° C. for 1–1.5 h, the ethanol produced was removed under reduced pressure, affording 16 g (100% yield) of the title compound.

$^1$H NMR (CDCl$_3$): δ 11.0 (1H, d); 8.43 (1H, d); 7.45–7.29 (5H, m); 6.87 (1H, d); 6.67 (1H, d); 6.64 (1H, dd); 5.14 (2H, s); 4.31 (2H, q); 25 (2H, q); 3.91 (3H, s); 1.39 (3H, t); 1.32 (3H, t).

d) Ethyl 6-benzyloxy-4-chloro-7-methoxy-3-quinolinecarboxylate

A mixture of diethyl 2-(4-(benzyloxy-3-methoxyanilino) methylenemalonate (16 g, 40 mmol), toluene (100 ml) and phosphorus oxychloride (25 ml) was heated to reflux under nitrogen atmosphere for 5 hours. After cooling, the solution was evaporated to remove the solvents and excess of phosphorus oxychloride. The residue was treated with aqueous sodium bicarbonate, water and some ethanol, heated to reflux for some minutes. After cooling the precipitate was filtered, washed three times with water and dried in vacuum at 50° C. to afford 12 g (81% yield) of the title compound.

$^1$H NMR (DMSO-d6): δ 8.97 (1H, s); 7.68 (1H, s); 7.55 (2H, bd); 7.53 (1H, s); 7.46–7.35 (3H, m); 5.34 (2H, s); 4.40 (2H, q); 4.00 (3H, s); 1.37 (3H, t).

e) 6-(Benzyloxy)-4-chloro-7-methoxy-3-quinolinecarboxylic acid

Ethyl 6-(Benzyloxy)-4-chloro-7-methoxy-3-quinolinecarboxylate (11.9 g, 32 mmol) was dissolved in a mixture of tetrahydrofurane (THF) and methanol (300 ml) in a ratio of 1:1. Aqueous sodium hydroxide (2.0 M, 65 ml, 130 mmol) was added and the mixture stirred at room temperature for 2 hours. The organic solvents were removed by rotatory evaporation and the resulting solution diluted with more water (200 ml) cooled on ice and acidified to pH 2–3 with hydrochloric acid under vigorous stirring. The precipitate was filtered off washed twice with water, twice with ethanol and ether and finally dried in vacuum at 50° C. over night to give a white solid, 11.0 g (100% yield).

$^1$H NMR (DMSO-d6): δ 13.66 (1H, bs); 8.97 (1H, s); 7.68 (1H, s); 7.54 (2H, bd); 7.52 (1H, s); 7.46–7.34 (3H, m); 5.34 (2H, s); 4.00 (3H, s).

f) 6-(Benzyloxy)-4-chloro-7-methoxy-3-quinolinecarboxamide

A mixture of 6-Benzyloxy-4-chloro-7-methoxy-3-quinolinecarboxylic acid (11.0 g, 32 mmol), thionyl chloride (30 ml) and toluene (100 ml) was refluxed for 2 hours under N$_2$ atmosphere.

After cooling toluene and the excess thionyl chloride was removed by rotatory evaporation and the residue was suspended in acetone (250 ml) and the resulting suspension cooled in an ice-bath. Aqueous ammonia (25%, 20 ml) was added gradually, keeping the temperature below 10° C. Stirring was continued for 3 hours and the acetone was then removed by rotatory evaporation. The residue was suspended in water (200 ml) and stirred for one hour, filtered off, washed twice with water, twice with ethanol and ether and finally dried in vacuum at 50° C. over night to give a offwhite solid, 10.4 g (95% yield).

$^1$H NMR (DMSO-d6): δ 8.65 (1H, s); 8.10 (1H, s); 7.83 (1H, s); 7.59 (1H, s); 7.54 (2H, bd); 7.50 (1H, s); 7.46–7.34 (3H, m); 5.33 (2H, s); 3.98 (3H, s).

g) 6-Benzyloxy-4-3-(hydroxymethyl-2-methylanilino)-7-methoxy-3-quinolinecarboxamide.

A mixture of 6-Benzyloxy-4-chloro-7-methoxy-3-quinolinecarboxamide (1.72 g, 5 mmol), 3-amino-2-methylbenzylalcohol (0.82 g, 6 mmol), acetic acid (1.2 ml) in DMF (20 ml) was heated at 100° C. for two hours. After cooling the reaction mixture was poured on ice-water (500 ml) and alcalized to pH 9 with dilute sodium hydroxide. The resulting precipitate was filtered off, washed with water, air dried, washed twice with ether and then dried in vacuum at 50° C. to give 2.15 g (97% yield) of the title compound as a white solid.

$^1$H NMR (CDCl$_3$): δ 10.82 (1H, s); 8.87 (1H, s); 8.26 (1H, s); 7.59 (1H, s); 7.37–7.20 (5H, m); 7.14–7.04 (3H, m); 6.73 (1H, s); 6.65 (1H, d); 5.22 (1H, t); 4.61 (2H, d); 4.50 (2H, s); 3.91 (3H, s); 2.20 (3H, s).

EXAMPLE 2

6-Hydroxy-4-3-(hydroxymethyl-2-methylanilino)-7-methoxy-3-quinolinecarboxamide

A mixture of 6-Benzyloxy-4-3-(hydroxymethyl-2-methylanilino)-7-methoxy-3-quinolinecarboxamide (2.1 g, 4.7 mmol) and 10% palladium on carbon (0.44 g) in methanol (50 ml), DMF (40 ml), ethylacetate (40 ml) and acetic acid (0.5 ml) was hydrogenolyzed at atmospheric pressure at 25° C. After 24 hours the reaction mixture was filtered through a plug of celite, which was subsequentely washed with DMF. The combined filtrates were alcalized with aqueous ammonia was added and the solvents were removed by reduced pressure. The residue was suspended in methanol (10 ml), filtered and washed with methanol and ether, dried in vacuum at 50° C. overnight to give 1.1 g (66% yield) of the title compound as a yellow solid.

$^1$H NMR (DMSO-d6): δ 10.43 (1H, s); 9.53 (1H, s); 8.85 (1H, s); 8.27 (1H, s); 7.60 (1H, s); 7.27 (1H, s); 7.08 (1H, d); 6.95 (1H, t); 6.78 (1H, s); 6.40 (1H, d); 5.13 (1H, t); 4.57 (2H, d); 3.92 (3H, s); 2.29 (3H, s).

EXAMPLE 3

4-(3-Hydroxymethyl-2-methylanilino)-7-methoxy-6-[3-(4-morpholinyl)propoxy]-3-quinolinecarboxamide A mixture of 6-hydroxy-4-(3-hydroxymethyl-2-methylanilino)-7-methoxy-3-quinolinecarboxamide (0.071 g, 0.20 mmol), 4-(3-chloropropyl)morpholine (0.036 g, 0.22 mmol), cesiumcarbonate (0.13 g, 0.40 mmol) and DMF (2.5 ml) was heated at 100° C. for two hours. After cooling the reaction mixture was poured on water and extracted three times with dichloromethane, the solvents were removed by reduced pressure and the residue was chromatographed on silica using dichloromethane/methanol/ammonia (200:10:1) as eluent.

Fractions containing the product (slightly impure) were combined and evaporated. The residue was triturated with the eluent affording 40 mg (38% yield) of the title compound as a white solid.

$^1$H NMR (CDCl$_3$): δ 10.91 (1H, s); 8.76 (1H, s); 7.26 (1H, s); 7.16 (1H, dd); 7.14 (1H, t); 7.04 (1H, dd); 6.74 (1H, s); 6.15 (2H, bs); 4.69 (2H, s); 3.95 (3H, s); 3.79 (4H, bt); 3.54 (2H, bt); 3.49 (1H, s); 2.46 (4H, m); 2.32 (2H, m); 2.30 (3H, s); 1.63 (2H, qv).

EXAMPLE 4

4-(3-Hydroxymethyl-2-methylanilino)-7-methoxy-6-(2-methoxyethoxy)-3-quinolinecarboxamide prepared according to the method described in Example 3

$^1$H NMR (DMSO-d6): δ 10.81 (1H, s); 8.87 (1H, s); 8.26 (1H, s); 7.59 (1H, s); 7.25 (1H, s); 7.19 (1H, d); 7.07 (1H, t); 6.67 (1H, d); 6.65 (1H, s); 5.15 (1H, t); 4.56 (2H, d); 3.89 (3H, s); 3.47 (2H, bt); 3.40 (2H, bt); 3.20 (3H, s); 2.26 (3H, s).

EXAMPLE 5

4-(3-Hydroxymethyl-2-methylanilino]-7-methoxy-6-octyloxy-3-quinolinecarboxamide prepared according to the method described in Example 3

$^1$H NMR (DMSO-d6): δ 10.89 (1H, s); 8.86 (1H, s); 8.25 (1H, s); 7.58 (1H, s); 7.22 (1H, s); 7.18 (1H, d); 7.07 (1H, t); 6.70 (1H, d); 6.65 (1H, s); 5.14 (1H, t); 4.55 (2H, d); 3.88 (3H, s); 3.32 (2H, bt); 2.24 (3H, s); 1.45 (2H, m); 1.33–1.15 (10H, m); 0.87 (3H, t).

EXAMPLE 6

4-(3-Hydroxymethyl-2-methylanilino)-7-methoxy-6-[2-(4-morpholinyl)ethoxy]-3-quinolinecarboxamide prepared according to the method described in Example 3

$^1$H NMR (DMSO-d6): δ 10.86 (1H, s); 8.87 (1H, s); 8.26 (1H, brs); 7.59 (1H, brs); 7.24 (1H, s); 7.18 (1H, d); 7.07 (1H, t); 6.68 (1H, d); 6.67 (1H, s); 5.15 (1H, t); 4.55 (2H, d); 3.88 (3H, s); 3.54 (4H, m); 3.45 (2H, brt); 2.43 (2H, t); 2.30 (4H, m); 2.24 (3H, s).

EXAMPLE 7

4-(3-Hydroxymethyl-2-methylanilino)-7-methoxy-6-[2-(1-piperidinyl)ethoxy]-3-quinolinecarboxamide prepared according to the method described in Example 3

$^1$H NMR (DMSO-d6): δ 10.84 (1H, s); 8.86 (1H, s); 8.25 (1H, brs); 7.57 (1H, brs); 7.22 (1H, s); 7.17 (1H, d); 7.05 (1H, t); 6.67 (1H, d); 6.65 (1H, s); 5.13 (1H, brs); 4.54 (2H, s); 3.86 (3H, s); 3.41 (2H, brt); 2.39 (2H, t); 2.25 (4H, m); 2.23 (3H, s); 1.45 (4H, m); 1.35 (2H, m).

EXAMPLE 8

4-(3-Hydroxymethyl-2-methylanilino)-7-methoxy-6-[2-(1-pyrrolidinyl)ethoxy]-3-quinolinecarboxamide prepared according to the method described in Example 3

$^1$H NMR (DMSOd6): δ 10.83 (1H, s); 8.87 (1H, s); 8.26 (1H, brs); 7.58 (1H, brs); 7.24 (1H, s); 7.18 (1H, d); 7.06 (1H, t); 6.67 (1H, s); 6.66 (1H, d); 5.16 (1H, brt); 4.55 (2H, d); 3.88 (3H, s); 3.44 (2H, brt); 2.51 (2H, m); 2.35 (4H, m); 2.26 (3H, s); 1.65 (4H, m).

EXAMPLE 9

6-[2-(Dimethylamino)ethoxy]-4-(3-hydroxymethyl-2-methylanilino)-7-methoxy-3-quinolinecarboxamide prepared according to the method described in Example 3

$^1$H NMR (DMSO-d6): δ 10.87 (1H, s); 8.88 (1H, s); 8.27 (1H, brs); 7.60 (1H, brs); 7.26 (1H, s); 7.19 (1H, d); 7.08 (1H, t); 6.69 (1H, d); 6.68 (1H, s); 5.14 (1H, brs); 4.56 (2H, s); 3.89 (3H, s); 3.51 (2H, brt); 2.62 (2H, brt); 2.26 (6H, s); 2.25 (3H, s).

EXAMPLE 10

6-[2-(Dimethylamino)-2-oxoethoxy]-4-(3-hydroxymethyl-2-methylanilino)-7-methoxy-3-quinolinecarboxamide prepared according to the method described in Example 3

$^1$H NMR DMSO(d6): δ 10.81 (1H, s); 8.89 (1H, s); 8.28 (1H, brs); 7.60 (1H, brs); 7.27 (1H, s); 7.17 (1H, d); 7.03 (1H, t); 6.58 (1H, d); 6.48 (1H, s); 5.18 (1H, brt); 4.57 (2H, d); 4.23 (2H, brs); 3.91 (3H, s); 2.74 (3H, s); 2.66 (3H, s); 2.22 (3H, s).

EXAMPLE 11

6-(2-Amino-2-oxoethoxy)-4-(3-hydroxymethyl-2-methylanilino)-7-methoxy-3-quinolinecarboxamide prepared according to the method described in Example 3

$^1$H NMR DMSO(d6): δ 10.71 (1H, s); 8.88 (1H, s); 8.26 (1H, brs); 7.59 (1H, brs); 7.27 (1H, s); 7.26 (1H, s); 7.18 (1H, d); 7.05 (1H, s); 7.03 (1H, t); 6.62 (1H, s); 6.58 (1H, d); 5.11 (1H, t); 4.57 (2H, d); 3.91 (3H, s); 3.85 (2H, s); 2.26 (3H, s).

EXAMPLE 12

4-(2-Ethylanilino)-6-methoxy-7-[3-(4-morpholinyl)propoxy]-3-quinolinecarboxamide a) 4-Chloro-7-hydroxy-6-methoxy-3-quinolinecarboxamide.

A mixture of 7-Benzyloxy-4-chloro-6-methoxy-3-quinolinecarboxamide (1.0 g, 2.9 mmol) prepared analogous to the method described in Example 1 and thioanisole (1.75 ml, 14.1 mmol) in TFA (15 ml) was refluxed for three hours. After cooling, the solvents were removed at reduced pressure and the residue was poured on water and alkalized with aqueous ammonia. The precipitate was filtered, washed with water and dried affording 0.52 g (72% yield) of the title compound.

b) 4-(2-Ethylanilino)-6-methoxy-7-[3-(4-morpholinyl)propoxy]-3-quinolinecarboxamide.

A mixture of 4-Chloro-7-hydroxy-6-methoxy-3-quinolinecarboxamide (0.056 g, 0.22 mmol), 2-ethylaniline (32 μL, 0.26 mmol) and acetic acid (10 μL) in ethanol (5 ml) was heated at reflux for four hours. The solvents were removed by reduced pressure and the residue was chromatographed on silica using methanol as eluent. The product was dissolved in DMSO (5 ml), morpholinopropylchloride (0.018 g, 0.11 mmol) and Cs$_2$CO$_3$ (0.090 g, 0.28 mmol) were added and the mixture was heated at 100° C. for 20 hours. After cooling the mixture was poured on water and the water phases were extracted with methylenechloride. The residue was chromatographed on silica using methylenechloride/methanol (9/1–1/1) as eluent, affording 9 mg (9% yield) of the titled compound. $^1$H NMR (CDCl$_3$): δ 11.05 (1H, s); 8.96 (1H, s); 7.35 (1H, s); 7.32 (1H, dd); 7.12 (2H, m); 6.91

(1H, dd); 6.74 (1H, s); 4.22 (2H, m); 3.68 (4H, m); 3.25 (3H, s); 2.80 (2H, m); 2.52 (2H, q); 2.44 (4H, m); 2.08 (2H, m); 1.30 (3H, t).

the title compounds of examples 13–15 were prepared by a method analogous to that described in Example 12.

EXAMPLE 13

6-Methoxy-4-[2-(methylsulfanyl)anilino]-7-[3-(4-morpholinyl)propoxy]-3-quinolinecarboxamide $^1$H NMR (CDCl$_3$): δ 10.76 (1H, s); 8.89 (1H, s); 7.34 (1H, s); 7.32 (1H, d); 7.11 (1H, dd); 7.02 (1H, dd); 6.79 (1H, d); 6.75 (1H, s); 4.21 (2H, t); 3.72 (4H, t); 3.39 (3H, s); 2.55–2.42 (6H, m); 2.49 (3H, s); 2.10–2.02 (2H, m).

EXAMPLE 14

4-[3-(Hydroxymethyl)-2-methylanilino]-6-methoxy-7-[3-(4-morpholinyl)propoxy]-3-quinolinecarboxamide $^1$H NMR (CDCl$_3$): δ 10.81 (1H, s); 8.79 (1H, s); 7.26 (1H, s); 7.20 (1H, d); 7.16 (1H, dd); 6.84 (1H, d); 6.69 (1H, s); 4.74 (2H, s); 4.15 (2H, t); 3.68 (4H, t); 3.29 (3H, s); 2.48 (2H, t); 2.42 (4H, m); 2.32 (3H, s); 2.01 (2H, m).

EXAMPLE 15

4-(1H-Indol-4-ylamino)-6-methoxy-7-[3-(4-morpholinyl)propoxy]-3-quinolinecarboxamide $^1$H NMR (CD$_3$OD): δ 8.82 (1H, s); 7.37 (1H, d); 7.23 (1H, d); 7.15 (1H, s); 7.14 (1H, t); 6.92 (1H, s); 6.88 (1H, d); 6.21 (1H, d); 4.21 (2H, t); 3.78 (4H, t); 2.98 (3H, s); 2.98–2.88 (6H, m); 2.18 (2H, m).

EXAMPLE 16

Methyl 4-{[3-(aminocarbonyl)-6-methoxy-4-(2-toluidino)-7-quinolinyl]oxy}butanoate A mixture of 7-hydroxy-6-methoxy-4-(2-toluidino)-3-quinolinecarboxamide (0.026 g, 0.080 mmol), DMSO (2.5 ml), K$_2$CO$_3$ (0.017 g, 0.12 mmol), and methyl 4-chlorobutanoate (0.011 g, 0.080 mmol) was refluxed for 2 h. The reactionmixture was filtered, evaporated and chromatographed on silica furnishing the title compound.

$^1$H-NMR DMSO-d6: δ 10.72 (1H, s); 8.85 (1H, s); 8.25 (1H, brs); 7.58 (1H, brs); 7.28 (1H, d); 7.22 (1H, s); 7.10–6.97 (2H, m); 6.68 (1H, d); 6.67 (1H, s); 4.10 (2H, t); 3.57 (3H, s); 3.26 (3H, s); 3.28 (3H, s); 2.05–1.93 (4H, m).

APCI-MS m/z: 424.1 [MH+]

EXAMPLE 17

4-(2-Ethylanilino)-7-(3-hydroxypropoxy)-6-methoxy-3-quinolinecarboxamide

A mixture of 4-(2-ethylanilino)-7-hydroxy-6-methoxy-3-quinolinecarboxamide (0.12 g, 0.35 mmol), DMSO (15 ml), Cs$_2$CO$_3$ (0.34 g, 1.0 mmol), and 1,3-dibromopropane was stirred at 100° C. for 2 h. The reaction mixture was poured out on NaHCO$_3$ (aq) and extracted with CH$_2$Cl$_2$. The substance was chromatographed on furnishing the title compound (0.012 g, 9%).

$^1$H NMR (CDCl$_3$): δ 10.82 (1H, s); 8.83 (1H, s); 7.34–7.26 (2H, m); 7.09 (1H, m); 6.83 (1H, dd); 6.70 (1H, s); 4.60 (2H, t); 3.93 (2H, t); 3.28 (3H, s); 2.77 (2H, q); 2.12 (2H, m); 1.22 (3H, t).

APCI-MS m/z: 396.1 [MH+]

EXAMPLE 18

6-Methoxy-7-[2-(4-morpholinyl)ethoxy]-4-(2-toluidino)-3-quinolinecarboxamide

The title compound was prepared according to the method described in Example 12.

$^1$H NMR (CDCl$_3$): δ 10.60 (1H, s); 8.72 (1H, s); 7.28–7.26 (2H, m); 7.07 (1H, m); 6.89 (1H, m); 6.75 (1H, s); 4.28 (2H, t); 3.72 (4H, t); 3.32 (3H, s); 2.88 (3H, t); 2.58 (4H, t); 2.36 (3H, s).

APCI-MS m/z: 437.2 [MH+]

EXAMPLE 19

4-(2-Ethylanilino)-6-methoxy-7-(2-methoxyethoxy)-3-quinolinecarboxamide

A mixture of 4-(2-ethylanilino)-7-hydroxy-6-methoxy-3-quinolinecarboxamide (0.22 g, 0.65 mmol), DMF (15 ml), Cs$_2$CO$_3$ (0.64 g, 1.98 mmol), and 2-bromoethylmethylether was stirred at 100° C. for 2 h. The reactionmixture was evaporated and chromatographed on furnishing the title compound (0.045 g, 18%.

$^1$H NMR (CDCl$_3$): δ 10.70 (1H, s); 8.72 (1H, s); 7.30 (1H, dd); 7.26 (1H, s); 7.08 (1H, m); 6.85 (1H, dd); 6.74 (1H, s); 4.28 (2H, t); 3.83 (2H, t); 3.45 (3H, s); 3.30 (3H, s); 2.80 (2H, q); 1.30 (3H, t).

APCI-MS m/z: 396.1 [MH+]

EXAMPLE 20

4-(2-Ethylanilino)-6-methoxy-7-[3-(1H-1,2,4-triazol-1-yl)propoxy]-3-quinolinecarboxamide a) Ethyl-3-(1H-1,2,4-triazol-1-yl)propanoate.

To a solution of 1H-1,2,4-triazole (5 g, 72.4 mmol), EtOH (36 ml) and Na (1.66 g, 72.4 mmol) ethyl-3-bromopropionat (9.9 ml, 79.6 mmol) was added dropwise. The reaction mixture was stirred overnight, filtered, evaporated to 50 ml and distilled furnishing the title compound (3.3 g 30%) as a white solid.

$^1$H NMR (DMSO-d6): δ 8.43 (1H, s); 7.90 (1H, s); 4.30 (2H, t); 3.94 (2H, q); 2.78 (2H, t); 1.05 (3H, t).

b) 3-(1H-1,2,4-triazol-1-yl)-1-propanol.

To a solution of Ethyl-3-(1H-1,2,4-triazol-1-yl)propanoate (2.95 g, 17.5 mmol) in ether (90 ml), LiAlH$_4$ (0.66 g, 17.5 mmol) was added. After heating to reflux for 60 h, 10 ml of 50%-methanol-water was added. The reaction mixture was filtered and the filter washed with 100 ml of methanol and twice with 100 ml of hot water. After evaporation the title product was obtained after purification using preparative HPLC.

¹H NMR (CDCl₃): δ 8.42 (1H, s); 7.98 (1H, s); 4.35 (2H, t); 3.47 (2H, t); 2.09 (2H, q).

c) 1-(3-Chloropropyl)-1H-1,2,4-triazole.

3-(1H-1,2,4-triazol-1-yl)-1-propanol (0.160 g, 1.3 mmol) was refluxed in thionylchloride (3 ml) for 2 h. The recation mixture was evaporated yielding the title product.

APCI-MS m/z: 146.1 [MH+]

d) 4-(2-Ethylanilino)-6-methoxy-7-[3-(1H-1,2,4-triazol-1-yl)propoxy]-3-quinolinecarboxamide.

The title product was prepared according to the method described in Example 17

¹H NMR (CDCl₃): δ 10.71 (1H, s); 8.70 (1H, s); 8.07 (1H, s); 7.94 (1H, s); 7.34–7.29 (1H, m); 7.20 (1H, s); 7.16–7.05 (2H, m); 6.90–6.85 (1H, m); 6.76 (1H, s); 4.44 (2H, t); 4.28 (2H, t); 3.62 (3H, s); 2.80 (2H, q); 2.46 (2H, m); 1.30 (3H, t).

APCI-MS m/z: 447.5 [MH+]

EXAMPLE 21

4-(2-Ethylanilino)-6-methoxy-7-[4-(4-morpholinyl)butoxy]-3-quinolinecarboxamide 4-(2-Ethylanilino)-7-hydroxy-6-methoxy-3-quinolinecarboxamide (0.064 g, 0.19 mmol) was dissolved in DMSO (4 ml), 1-bromo-4-chlorobutane (22 μl, 0.19 mmol) and Cs₂CO₃ (0.18 g, 0.55 mmol) were added and the mixture was stirred at ambient temperature for three days. The mixture was poured into water and extracted with methylenechloride. The residue was chromatographed on silica using ethylacetate/methanol (1:0–>1:1) as eluent. The resulting oil was dissolved in DME, morpholine (25 μl, 0.29 mmol) and a catalytic ammount of KI was added, mixture was heated at reflux for four days. After cooling the mixture was poured out on water and extracted with methylenechloride. The crude product was purified on preparative HPLC, affording 20 mg (22% yield) of the titled compound.

¹H NMR (CDCl₃): δ 11.31 (1H, s); 9.02 (1H, s); 7.40 (1H, s); 7.34 (1H, d); 7.22–7.11 (2H, m); 6.95 (1H, d); 6.73 (1H, s); 4.18 (2H, t); 3.72 (4H, m); 3.29 (3H, s); 2.79 (2H, q); 2.5–2.40 (6H, m); 1.93 (2H, m); 1.69 (2H, m); 1.28 (3H, t).

EXAMPLE 22 a) 7-(3-Chloropropoxy)-4-[3-(hydroxymethyl)-2-methylanilino]-6-methoxy-3-quinolinecarboxamide.

7-Hydroxy-4-[3-(hydroxymethyl)-2-methylanilino]-6-methoxy-3-quinolinecarboxamide (0.90 mg, 2.54 mmol) was dissolved in DMF (10 ml), 1-bromo-4-chlorobutane (0.28 ml, 2.79 mmol) and Cs₂CO₃ (1.7 g, 5.2 mmol) were added and the mixture was stirred at ambient temperature for three days. The mixture was poured out on water and extracted with methylenechloride. The residue was chromatographed on silica using ethylacetate/methanol (1:0–>5:1) as eluent, affording 550 mg (50% yield) of the titled compound.

¹H NMR (DMSO-d6): δ 10.85 (1H, s); 8.83 (1H, s); 8.22 (1H, s, br); 7.30 (1H, s, br); 7.22 (1H, s); 7.10 (1H, d); 7.02 (1H, t); 6.65 (1H, d); 6.62 (1H, s); 5.18 (1H, m); 4.58 (2H, d); 4.21 (2H, t); 3.78 (2H, t); 3.22 (3H, s); 2.23 (3H, s); 2.23–2.19 (2H, m).

EXAMPLE 23a, 23b

7-{3-[(cis)-2,6-Dimethylmorpholinyl]propoxy}-4-[3-(hydroxymethyl)-2-methylanilino]-6-methoxy-3-quinolinecarboxamide and 7-{3-[(trans)-2,6-Dimethylmorpholinyl]propoxy}-4-[3-(hydroxymethyl)-2-methylanilino]-6-methoxy-3-quinolinecarboxamide 7-(3-chloropropoxy)-4-[3-(hydroxymethyl)-2-methylanilino]-6-methoxy-3-quinolinecarboxamide (50 mg, 0.12 mmol) was dissolved in DME (3 ml), 2,6-dimethylmorpholine (25 μl, 0.29 mmol) and a catalytic ammount of KI added, the mixture was heated at reflux for four days. After cooling the mixture was filtrated and the crude product was purified on preparative HPLC, affording 14 mg (23% yield) of the cis-compound and 8 mg (13% yield) of the trans-compound.

7-{3-[(cis)-2,6-dimethylmorpholinyl]propoxy}-4-[3-(hydroxymethyl)-2-methylanilino]-6-methoxy-3-quinolinecarboxamide:

¹H NMR (CD₃OD): δ 8.89 (1H, s); 7.24 (1H, d); 7.20 (1H, s); 7.18 (1H, t); 6.95 (1H, d); 6.79 (1H, s); 4.68 (2H, s); 4.20 (2H, t); 3.75–3.65 (2H, m); 3.29 (3H, s); 3.0 (2H, d); 2.78 (2H, t); 2.38 (3H, s); 2.16 (2H, m); 1.95 (2H, m); 1.18 (6H, d).

7-{3-[(trans)-2,6-dimethylmorpholinyl]propoxy}-4-[3-(hydroxymethyl)-2-methylanilino]-6-methoxy-3-quinolinecarboxamide:

¹H NMR CD₃OD, at 55° C.: δ 8.82 (1H, s); 7.52 (1H, d); 7.35 (1H, t); 7.29 (1H, s); 7.18 (1H, d); 6.85 (1H, s); 4.78 (2H, s); 4.30 (2H, t); 4.18 (2H, m); 3.35 (3H, s); 3.21 (4H, m); 2.93 (2H, m); 2.34 (2H, m); 2.35 (3H, s); 1.35 (6H, d).

the title compounds of example 24–26 were prepared by a method analogous to that described in Example 23

EXAMPLE 24

4-[3-(Hydroxymethyl)-2-methylanilino]-6-methoxy-7-[3-(1-piperidinyl)propoxy]-3-quinolinecarboxamide ¹H NMR (CD₃OD): δ 8.82 (1H, s); 7.34 (1H, d); 7.25 (1H, s); 7.18 (1H, t); 6.89 (1H, d); 6.85 (1H, s); 4.75 (2H, s); 4.22 (2H, t); 3.35 (3H, s); 3.20–3.05 (6H, m); 2.40 (3H, s); 2.28 (2H, m); 1.85 (4H, m); 1.64 (2H, m).

EXAMPLE 25

7-{3-[(2-Ethoxyethyl)amino]propoxy}-4-[3-(hydroxymethyl)-2-methylanilino]-6-methoxy-3-quinolinecarboxamide ¹H NMR (CD₃OD): δ 8.82 (1H, s); 7.30 (1H, d); 7.25 (1H, s); 7.18 (1H, t); 6.89 (1H, d); 6.82 (1H, s); 4.76 (2H, s); 4.22 (2H, t); 3.59 (2H, t); 3.53 (2H, q); 3.35 (3H, s); 2.89 (2H, t); 2.83 (2H, t); 2.40 (3H, s); 2.12 (2H, m); 1.18 (3H, t).

EXAMPLE 26

4-[3-(Hydroxymethyl)-2-methylanilino]-6-methoxy-7-[3-(4-thiomorpholinyl)propoxy]-3-quinolinecarboxamide $^1$H NMR (CD$_3$OD): δ 8.81 (1H, s); 7.31 (1H, d); 7.22 (1H, s); 7.18 (1H, t); 6.86 (1H, d); 6.80 (1H, s); 4.75 (2H, s); 4.20 (2H, t); 3.38 (3H, s); 3.08 (2H, m); 2.80–2.60 (8H, m); 2.39 (3H, s); 2.08 (2H, m).

EXAMPLE 27

6-[3-(Dimethylamino)propoxy]-4-(2-ethylanilino)-7-methoxy-3-quinolinecarboxamide a) 6-(Benzyloxy)-4-(2-ethylanilino)-7-methoxy-3-quinolinecarboxamide The title compound was prepared according to the method described in Example 1g APCI-MS m/z: 428 [MH+]

b) 4-(2-Ethylanilino)-6-hydroxy-7-methoxy-3-quinolinecarboxamide

The title compound was prepared according to the method described in Example 2

$^1$H NMR (DMSO-d6): δ 10.52 (1H, s); 9.54 (1H, brs); 8.86 (1H, s); 8.29 (1H, brs); 7.62 (1H, brs); 7.28 (1H, s); 7.28 (1H, m); 6.98 (2H, m); 6.76 (1H, s); 6.45 (1H, m); 3.92 (3H, s); 2.75 (2H, q); 1.29 (3H, t).

APCI-MS m/z: 338 [MH+]

c) 6-[3-(Dimethylamino)propoxy]-4-(2-ethylanilino)-7-methoxy-3-quinolinecarboxamide Polymer-bound Triphenylphosphine (0.15 g, 0.44 mmol) and 3-dimethylamino-1-propanol (26 μl, 0.22 mmol) was suspended and dissloved in CH$_2$Cl$_2$ and THF at −15° C. and stirred for 30 min. DEAD (70 μl, 0.44 mmol) was added dropwise at −15° C. 4-(2-Ethylanilino)-6-hydroxy-7-methoxy-3-quinolinecarboxamide (50 mg, 0.15 mmol) was suspended in THF and then added to the reaction. The reaction was stirred over night, allowing the temperature rise to ~10° C. The polymer was filtered off and the filtrate concentrated in vacuo. The product was purified using preparative HPLC according 15 mg (24%) of white crystals.

$^1$H NMR (CD$_3$OC): δ 8.79 (1H, s); 7.37 (1H, m); 7.22 (1H, s); 7.15 (2H, m); 6.84 (1H, m); 6.78 (1H, s); 3.95 (3H, s); 3.42 (2H, t); 2.79 (2H, q); 2.35 (2H, t); 2.23 (6H, s); 1.74 (2H, m); 1.29 (3H, t)

APCI-MS m/z: 423 [MH+]

the title compounds of examples 28–33 were prepared by a method analogous to that described in Example 27

EXAMPLE 28

4-(2-Ethylanilino)-6-[3-(1H-imidazol-1-yl)propoxy]-7-methoxy-3-quinolinecarboxamide $^1$H NMR (CD$_3$OD): δ 8.80 (1H, s); 7.54 (1H, s); 7.29 (1H, m); 7.24 (1H, s); 7.06 (3H, m); 6.98 (1H, s); 6.80 (1H, m); 6.71 (1H, s); 3.99 (3H, s); 3.28 (2H, m); 2.75 (2H, q); 2.04 (2H, m); 1.27 (3H, t)

APCI-MS m/z: 446 [MH+]

EXAMPLE 29

4-(2-Ethylanilino)-7-methoxy-6-(3-thienylmethoxy)-3-quinolinecarboxamide $^1$H NMR (CD$_3$OD): δ 8.80 (1H, s); 7.37 (2H, m); 7.24 (1H, s); 7.16 (2H, m); 7.06 (1H, m); 6.91 (1H, m); 6.87 (1H, s); 6.83 (1H, m); 4.53 (2H, s); 3.97 (3H, s); 2.76 (2H, q); 1.29 (3H, t)

APCI-MS m/z: 434 [MH+]

EXAMPLE 30

6-[2-(Dimethylamino)ethoxy]-4-(2-ethylanilino)-7-methoxy-3-quinolinecarboxamide $^1$H NMR (CD$_3$OD): δ 8.80 (1H, s); 7.37 (1H, m); 7.22 (1H, s); 7.15 (2H, m); 6.84 (1H, m); 6.78 (1H, m); 3.95 (3H, s); 3.50 (2H, brt); 2.80 (2H, q); 2.57 (2H, t); 2.24 (6H, s); 1.30 (3H, t).

APCI-MS m/z: 409 [MH+]

EXAMPLE 31

6-(3-Aminopropoxy)-4-(2-ethylanilino)-7-methoxy-3-quinolinecarboxamide

The compound was synthesized as above, using Boc-amino protected alcohol. After flitering off the polymer and evaporation, the residue was dissolved in CH$_2$Cl$_2$ and TFA (50:50) and stirred at room temperature for 30 min. The solvent was evaporated and the product was purified by preparative HPLC.

$^1$H NMR (CD$_3$OD): δ 8.82 (1H, s); 7.38 (1H, m); 7.23 (1H, s); 7.16 (2H, m); 6.86 (1H, m); 6.80 (1H, s); 3.97 (3H, s); 3.48 (2H, brt); 2.81 (2H, q); 2.71 (2H, t); 1.74 (2H, m); 1.31 (3H, t)

APCI-MS m/z: 395 [MH+]

EXAMPLE 32

4-(2-Ethylanilino)-7-methoxy-6-[2-(methylamino)ethoxy]-3-quinolinecarboxamide $^1$H NMR (CD$_3$OD): δ 8.80 (1H, s); 7.36 (1H, m); 7.23 (1H, s); 7.15 (2H, m); 6.84 (1H, m); 6.80 (1H, s); 3.97 (3H, s); 3.50 (2H, brt); 2.79 (2H, q); 2.75 (2H, t); 2.37 (3H, s); 1.29 (3H, t).

APCI-MS m/z: 395 [MH+]

EXAMPLE 33

6-(2-Aminoethoxy)-4-(2-ethylanilino)-7-methoxy-3-quinolinecarboxamide $^1$H NMR (CD$_3$OD): δ 8.80 (1H, s); 7.36 (1H, brd); 7.23 (1H, s); 7.14 (2H, m); 6.84 (1H, brd); 6.78 (1H, s); 3.96 (3H, s); 3.41 (2H, brt); 2.79 (4H, m); 1.29 (3H, t)

APCI-MS m/z: 381 [MH+]

EXAMPLE 34

7-[3-(Dimethylamino)propoxy]-4-(2-ethylanilino)-6-methoxy-3-quinolinecarboxamide a) 4-(2-Ethylanilino)-7-benzyloxy-6-methoxy-3-quinolinecarboxamide The title compound was prepared as described in Example 27a starting from 7-benzyloxy-4-chloro-6-methoxy-3-quinolinecarboxamide prepared analogous to the method described in Example 1. Yield 4.4 g (89%) of a light brown powder.

$^1$H NMR (DMSO-d6): δ 11.85 (1H, brs); 8.98 (1H, s); 8.47 (1H, brs); 7.84 (1H, brs); 7.52–7.33 (7H, m); 7.29–7.17 (2H, m); 6.99 (1H, brd); 6.75 (1H, s); 5.26 (2H, s); 3.24 (3H, s); 2.70 (2H, q); 1.20 (3H, t).

APCI-MS m/z: 428 [MH+]

b) 4-(2-Ethylanilino)-7-hydroxy-6-methoxy-3-quinolinecarboxamide

The title compound was prepared as described in Example 27b

Yield 0.3 g (90%) of a yellow oil that crystallizes after a few hours.

$^1$H NMR (CD$_3$OD): δ 8.70 (1H, s); 7.39 (1H, m); 7.19 (2H, m); 7.00 (1H, s); 6.94 (1H, m); 6.73 (1H, s); 2.78 (2H, q); 1.29 (3H, t).

APCI-MS m/z: 338 [MH+]

c) 7-[3-(Dimethylamino)propoxy]-4-(2-ethylanilino)-6-methoxy-3-quinolinecarboxamide The title compound was prepared as described in Example 27c.

$^1$H NMR (CD$_3$OD): δ 8.78 (1H, s); 7.35 (1H, m); 7.19 (1H, s); 7.13 (2H, m); 6.83 (1H, m); 6.77 (1H, s); 4.15 (2H, t); 3.28 (3H, s); 2.79 (2H, q); 2.57 (2H, t); 2.29 (6H, s); 2.05 (2H, m); 1.28 (3H, t).

APCI-MS m/z: 423 [MH+]

the title compounds of examples 35–37 were prepared by a method analogous to that described in Example 34

EXAMPLE 35

4-(2-Ethylanilino)-6-methoxy-7-{3-[methyl(4-pyridinyl)amino]propoxy}-3-quinolinecarboxamide $^1$H NMR (CD$_3$OD): δ 8.78 (1H, s); 7.93 (2H, brm); 7.37 (1H, m); 7.16 (2H, m); 7.13 (1H, s); 6.84 (1H, m); 6.79 (1H, s); 6.67 (2H, brd); 4.12 (2H, t); 3.65 (2H, t), 3.33 (3H, s); 3.01 (3H, s); 2.80 (2H, q); 2.13 (2H, m); 1.31 (3H, t).

APCI-MS m/z: 486 [MH+]

EXAMPLE 36

4-(2-Ethylanilino)-6-methoxy-7-{2-[methyl(4-pyridinyl)amino]ethoxy}-3-quinolinecarboxamide $^1$H NMR (CDCl$_3$): δ 11.11 (1H, s); 8.88 (1H, s); 8.20 (2H, brs); 7.33 (1H, d); 7.32 (1H, s); 7.15 (2H, m); 6.90 (1H, d); 6.75 (1H, d); 6.74 (1H, s); 4.36 (2H, t); 3.94 (2H, t); 3.23 (3H, s); 3.19 (3H, s); 2.78 (2H, q); 1.29 (3H, t).

APCI-MS m/z: 472 [MH+]

EXAMPLE 37

4-(2-Ethylanilino)-6-methoxy-7-[2-(methylamino)ethoxy]-3-quinolinecarboxamide $^1$H NMR (CD$_3$OD): δ 8.80 (1H, s); 7.37 (1H, m); 7.23 (1H, s); 7.15 (2H, m); 6.86 (1H, m); 6.80 (1H, s); 4.24 (2H, t); 3.30 (3H, s); 3.04 (2H, t); 2.80 (2H, q); 2.47 (3H, s); 1.29 (3H, t).

APCI-MS m/z: 395 [MH+]

EXAMPLE 38

4-(2-Ethylanilino)-6-methoxy-7-[2-(1-piperazinyl)ethoxy]-3-quinolinecarboxamide Triphenylphosphine (0.12 g, 0.44 mmol) and 1-(2-hydroxyethyl)piperazine (25 µl, 0.22 mmol) was dissloved in CH$_2$Cl$_2$ and THF at −15° C. and stirred for 30 min. DEAD (70 µl, 0.44 mmol) was added dropwise at −15° C. 4-(2-ethylanilino)-7-hydroxy-6-methoxy-3-quinolinecarboxamide (0.50 g, 0.15 mmol) was suspended in THF and then added to the reaction. The reaction was stirred over night, allowing the temperature rise to ~10° C. The solvent was removed under reduced pressure and the product was purified using preparative HPLC affording 34 mg (24%) of a clear oil.

$^1$H NMR (CD$_3$OD): δ 8.80 (1H, s); 7.36 (1H, m); 7.21 (1H, s); 7.13 (2H, m); 6.83 (1H, m); 6.77 (1H, s); 4.28 (2H, t); 3.28 (3H, s); 2.86 (6H, m); 2.79 (2H, q); 2.62 (4H, brs); 1.29 (3H, t).

APCI-MS m/z: 450 [MH+]

the title compounds of examples 39–41 were prepared by a method analogous to that described in Example 38

EXAMPLE 39

4-(2-Ethylanilino)-7-[3-(1H-imidazol-1-yl)propoxy]-6-methoxy-3-quinolinecarboxamide $^1$H NMR (CD$_3$OD): δ 8.79 (1H, s); 7.64 (1H, s); 7.37 (1H, m); 7.15 (3H, m); 6.95 (1H, s); 6.84 (1H, m); 6.79 (1H, s); 4.26 (2H, t); 4.06 (2H, t); 3.31 (3H, s); 2.80 (2H, q); 2.32 (2H, m); 1.29 (3H, t).

APCI-MS m/z: 446 [MH+]

EXAMPLE 40

4-(2-Ethylanilino)-7-[2-(1H-imidazol-1-yl)ethoxy]-6-methoxy-3-quinolinecarboxamide $^1$H NMR (CD$_3$OD): δ 8.78 (1H, s); 7.75 (1H, s); 7.36 (1H, m); 7.25 (1H, s); 7.17 (1H, s); 7.13 (2H, m); 6.93 (1H, s); 6.83 (1H, m); 6.78 (1H, s); 4.48 (2H, t); 4.36 (2H, t); 3.29 (3H, s); 2.78 (2H, q); 1.28 (3H, t).

EXAMPLE 41

7-(3-Aminopropoxy)-4-(2-ethylanilino)-6-methoxy-3-quinolinecarboxamide

The compound was synthesized as above, using Boc-amino protected alcohol. After flitering off the polymer and evaporation, the residue was dissolved in $CH_2Cl_2$ and TFA (50:50) and stirred at room temperature for 30 min. The solvent was evaporated and the product was purified by preparative HPLC.

$^1$H NMR ($CD_3OD$): δ 8.79 (1H, s); 7.36 (1H, m); 7.20 (1H, s); 7.13 (2H, m); 6.83 (1H, m); 6.77 (1H, s); 4.21 (2H, t); 3.28 (3H, s); 2.88 (2H, t); 2.79 (2H, q); 2.03 (2H, m); 1.29 (3H, t).

APCI-MS m/z: 395 [MH+]

EXAMPLE 42

7-Hydroxy-4-[3-(hydroxymethyl)-2-methylanilino]-6-methoxy-3-quinolinecarboxamide The title compound was prepared according to the method described in Example 34b.

$^1$H NMR (DMSO-d6): δ 10.86 (1H, s); 8.81 (1H, s); 8.21 (1H, brs); 7.54 (1H, brs); 7.18 (1H, d); 7.12 (1H, s); 7.08 (1H, t); 6.69 (1H, d); 6.65 (1H, s); 5.14 (1H, brs); 4.56 (2H, s); 3.25 (3H, s); 2.25 (3H, s)

APCI-MS m/z: 354 [MH+]

EXAMPLE 43

6-{[3-(1H-imidazol-1-yl)propyl]amino}-7-methoxy-4-(2-toluidino)-3-quinolinecarboxamide a) Ethyl 4-Chloro-6-bromo-7-methoxy-3-quinolinecarboxamide The title compound were prepared essentially as described by Burke, et al. *J. Med. Chem*, 36(1993)425–432.

b) Ethyl 6-bromo-7-methoxy-3-quinolinecarboxamide (0.90 g, 2.6 mmol), o-toluidine (0.30 ml, 2.9 mmol) and AcOH (1 ml) was dissolved in EtOH (50 ml) and refluxed for 4 hrs. After cooling the mixture was neutralised with aqueous ammonia and the precipitate was filtered off affording 870 mg (80%) of a green powder.

$^1$H NMR (DMSO-d6): δ 9.84 (1H, s); 8.94 (1H, s); 7.89 (1H, s); 7.41 (1H, s); 7.36 (1H, brd); 7.16 (2H, m); 6.94 (1H, brd); 4.15 (2H, q); 3.99 (3H, s); 2.28 (3H, s); 1.26 (3H, t).

c) 6-{[3-(1H-imidazol-1-yl)propyl]amino}-7-methoxy-4-(2-toluidino)-3-quinolinecarboxamide A mixture of 6-bromoquinoline (0.25 mmol), $Pd_2(dba)_3$ (0.005 mmol), BINAP (0.015 mmol), $Cs_2CO_3$ (0.33 mmol) and 1-(3-aminopropyl)-imidazole (0.29 mmol) was stirred at 90° C. over night under $N_2$. After cooling the mixture was purified by flash silica gel column chromatography. Elution with $CH_2Cl_2$ and then $CH_2Cl_2$/MeOH (10:1) gave 110 mg (100%) of a yellow oil which contained minor phosphine impurities.

APCI-MS m/z: 460 [MH+]

The crude ethylester was hydrolysed in MeOH/5M NaOH (1:1) at r.t. over night. After concentrating in vacuo, the remaining aqueous phase was made acidic with 2M HCl and washed with $CH_2Cl_2$. The aqueous phase was neutralised with 5M $Na_2CO_3$ and extracted with $CHCl_3$. Concentrating in vacuo gave 25 mg (25%) of a yellow oil.

APCI-MS m/z: 432 [MH+]

The crude acid (0.025 g, 0.06 mmol) and CDI (0.020 g, 0.1 mmol) was dissolved in DMF and stirred at 60° C. for 1 h. The mixture was cooled in a EtOH/dry ice bath and saturated with $NH_3$(g) and then stirred at room temperature for 45 minutes. The mixture was diluted with $CHCl_3$, washed with saturated aqueous $NaHCO_3$ and water and concentrated in vacuo. Purification with preparative HPLC gave after removal of the trifluoroacetate salt 15 mg (60%) of a white solid.

$^1$H NMR ($CD_3OD$): δ 8.67 (1H, s); 7.56 (1H, s, Im); 7.27 (1H, brd); 7.13 (1H, s); 7.02 (1H, s, Im); 6.97 (1H, s, Im); 6.95 (2H, m); 6.68 (1H, brd); 6.28 (1H, s); 3.99 (3H, s); 3.90 (2H, t); 2.67 (2H, t); 2.36 (3H, s); 1.68 (2H, m)

APCI-MS m/z: 431 [MH+]

the title compounds of examples 44–46 were prepared by a method analogous to that described in Example 43

EXAMPLE 44

7-Methoxy-6-[(2-methoxyethyl)amino]-4-(2-toluidino)-3-quinolinecarboxamide $^1$H NMR ($CD_3OD$): δ 8.66 (1H, s); 7.31 (1H, m); 7.11 (1H, s); 7.10 (2H, m); 6.81 (1H, m); 6.34 (1H, s); 4.00 (3H, s); 3.27 (3H, s); 3.24 (2H, t); 2.77 (2H, t); 2.35 (3H, s).

APCI-MS m/z: 381 [MH+]

EXAMPLE 45

7-Methoxy-6-{[2-(4-morpholinyl)ethyl]amino}-4-(2-toluidino)-3-quinolinecarboxamide $^1$H NMR (DMSO-d6): δ 10.41 (1H, s); 8.74 (1H, s); 8.23 (1H, brs); 7.56 (1H, brs); 7.25 (1H, d); 7.17 (1H, s); 6.96 (2H, m); 6.50 (1H, s); 6.22 (1H, d); 5.43 (1H, t); 3.95 (3H, s); 3.42 (4H, brt); 2.71 (2H, q); 2.33 (3H, s); 2.19 (6H, m).

APCI-MS m/z: 436 [MH+]

EXAMPLE 46

7-Methoxy-6-{[3-(4-morpholinyl)propyl]amino}-4-(2-toluidino)-3-quinolinecarboxamide $^1$H NMR ($CD_3OD$): δ 8.65 (1H, s); 7.27 (1H, brd); 7.11 (1H, s); 7.03 (2H, m); 6.72 (1H, brd); 6.32 (1H, s); 3.99 (3H, s); 3.69 (4H, t); 2.68 (2H, t); 2.39 (4H, brm); 2.37 (3H, s); 2.27 (2H, t); 1.49 (2H, m).

APCI-MS m/z: 450 [MH+]

EXAMPLE 47

6-Methoxy-7-{[2-(4-morpholinyl)ethyl]amino}-4-(2-toluidino)-3-quinolinecarboxamide a) Ethyl 4-Chloro-7-bromo-6-methoxy-3-quinolinecarboxamide The title compound were prepared essentially as described by Burke, et al., *J. Med. Chem*, 36(1993)425–432.

b) Ethyl 7-bromo-6-methoxy-4-(2-toluidino)-3-quinolinecarboxamide

The title compound was prepared according to the method described in Example 43b ¹H NMR (DMSO-d6): δ 9.83 (1H, s); 8.87 (1H, s); 8.15 (1H, s); 7.38 (1H, m); 7.17 (2H, m); 7.09 (1H, s); 6.98 (1H, m); 4.17 (2H, q); 3.45 (3H, s); 2.30 (3H, s); 1.28 (3H, t)

c) 6-Methoxy-7-{[2-(4-morpholinyl)ethyl]amino}-4-(2-toluidino)-3-quinolinecarboxamide The title compound was prepared according to the method described in Example 43c.

¹H NMR (CD₃OD): δ 8.68 (1H, s); 7.28 (1H, brd); 7.06 (2H, m); 6.81 (1H, brd); 6.73 (1H, s); 6.60 (1H, s); 3.67 (4H, brt); 3.34 (2H, t); 3.33 (3H, s); 2.65 (2H, t); 2.49 (4H, brt); 2.31 (3H, s).

APCI-MS m/z: 436 [MH+]

the title compounds of examples 48–51 were prepared by a method analogous to that described in Example 47

EXAMPLE 48

6-Methoxy-7-[(2-methoxyethyl)amino]-4-(2-toluidino)-3-quinolinecarboxamide

¹H NMR (CDCl₃): δ 10.50 (1H, s); 8.73 (1H, s); 7.25 (1H, brd); 7.04 (2H, m); 6.88 (1H, s); 6.87 (1H, brd); 6.63 (1H, s); 5.06 (1H, brt); 3.66 (2H, t); 3.42 (2H, q); 3.39 (3H, s); 3.34 (3H, s); 2.37 (3H, s)

APCI-MS m/z: 381 [MH+]

EXAMPLE 49

7-{[3-(1H-imidazol-1-yl)propyl]amino}-6-methoxy-4-(2-toluidino)-3-quinolinecarboxamide ¹H NMR (CDCl₃): δ 10.93 (1H, brs); 8.93 (1H, s); 7.51 (1H, s); 7.27 (1H, brd); 7.09 (2H, m); 7.06 (1H, s); 6.93 (1H, brd); 6.91 (1H, s); 6.90 (1H, s); 6.62 (1H, s); 4.81 (1H, brt); 4.06 (2H, t); 3.32 (3H, s); 3.25 (2H, m); 2.35 (3H, s); 2.16 (2H, m).

APCI-MS m/z: 431 [MH+]

EXAMPLE 50

7-[(1-Benzyl-4-piperidinyl)amino]-6-methoxy-4-(2-toluidino)-3-quinolinecarboxamide ¹H NMR (CD₃OD): δ 8.68 (1H, s); 7.32 (6H, m); 7.09 (2H, m); 6.85 (1H, brd); 6.78 (1H, s); 6.65 (1H, s); 3.59 (2H, s); 3.49 (1H, m); 3.35 (3H, s); 2.93 (2H, brd); 2.34 (3H, s); 2.28 (2H, brt); 2.08 (2H, brd); 1.60 (2H, m).

APCI-MS m/z: 496 [MH+]

EXAMPLE 51

6-Methoxy-6-{[3-(4-morpholinyl)propyl]amino}-4-(2-toluidino)-3-quinolinecarboxamide ¹H NMR (CD₃OD): δ 8.67 (1H, s); 7.31 (1H, brd); 7.11 (2H, m); 6.89 (1H, s); 6.70 (1H, s); 6.61 (1H, s); 4.84 (3H, s); 3.33 (3H, s); 3.30 (2H, t); 2.49 (2H, t); 2.46 (4H, brt); 2.32 (3H, s); 1.87 (2H, m).

APCI-MS m/z: 450 [MH+]

EXAMPLE 52

4-[3-(Hydroxymethyl)-2-methylanilino]-6,7-dimethoxy-3-quinolinecarboxamide a) Ethyl 6,7-dimethoxy-4-chloro-3-quinolinecarboxylate The title compound were prepared essentially as described by Burke, et al. *J. Med. Chem,* 36(1993)425–432.

b) 6,7-Dimethoxy-4-chloro-3-quinolinecarboxamide

A mixture of ethyl 6,7-dimethoxy-4-chloro-3-quinolinecaroxylate (3.0 g, 10.2 mmol) was dissolved in 40 ml methanol and NaOH(aq) (20 ml, 5M). The mixture was heated to 100° C. for four hours. After cooling the methanol was evaporated. The water solution was acidified with 2M HCl to pH 2–3. The white precipitate was cenrifuged and then decant. This procedure was repeated twice. The solid was dried in vacuum over night. The solid was dissolved in 50 ml thionyl chloride and heated to reflux for three hours. After cooling the excess thionylchloride was removed by rotary evaporation and the residue was suspended in acetone, the resulting suspension was cooled in an ice-bath. Ammonium hydroxide (7 ml) was added, keeping the temperature below 0° C. The suspension was stirred for 30 min and the resulting suspension was filtered off, washed with water and air dried.

¹H NMR (DMSO-d6): δ 8.66 (1H, s); 8.12 (1H, br s); 7.87 (1H, br s); 7.46 (2H, d); 3.98 (3H, s); 3.97 (3H, s).

c) 4-[3-(Hydroxymethyl)-2-methylanilino]-6,7-dimethoxy-3-quinolinecarboxamide.

A mixture of 4-chloro-6,7-dimethoxy-3-quinolinecarboxamide (0.15 g, 0.56 mmol), 3-amino-2-methylbenzylalcohol (0.1 g, 0.73 mmol), acetic acid (0.2 ml) in EtOH (10 ml) was refluxed for 4 h. After cooling the pH was adjusted to 9 with aqueous NH₃. The resulting precipitate was filtered off and washed with cold EtOH and dried in vaccum at 40° C. to give 0.1 g (49% yield) of the title compound.

¹H NMR (DMSO-d6): δ 10.84 (1H, s); 8.83 (1H, s); 8.25 (1H, s); 7.56 (1H, s); 7.21 (1H, s); 7.17 (1H, d); 7.05 (1H, t); 6.17 (1H, d); 6.15 (1H, s); 5.12 (1H, brs); 4.52 (2H, s); 3.87 (3H, s); 3.21 (3H, s); 2.23 (3H, s).

APCI-MS m/z: 368.2 [MH+]

the title compounds of examples 53–56 were prepared by a method analogous to that described in Example 52.

EXAMPLE 53

4-(2-Bromoanilino)-6,7-dimethoxy-3-quinolinecarboxamide

¹H NMR (CDCl₃): δ 10.28 (1H, s); 8.80 (1H, s); 7.63 (1H, d); 7.34 (1H, s); 7.21 (1H, s); 7.10 (1H, t); 7.05 (1H, t); 6.90 (1H, t); 6.75 (1H, s); 6.72 (1H, s); 4.0 (3H, s); 3.48 (3H, s).

APCI-MS m/z: 402.1, 404.1 [MH+]

EXAMPLE 54

4-(4-Hydroxy-2-methylanilino)-6,7-dimethoxy-3-quinolinecarboxamide

¹H NMR (DMSO-d6): δ 10.81 (1H, s); 9.30 (1H, s); 8.79 (1H, d); 8.18 (1H, brs); 7.45 (1H, brs); 7.19 (1H, s); 6.75–6.50 (4H, m); 3.84 (3H, s); 3.26 (3H, s); 2.32 (3H, s).

APCI-MS m/z: 354.1 [MH+]

EXAMPLE 55

6,7-Dimethoxy-4-(2-methoxyanilino)-3-quinolinecarboxamide $^1$H NMR (DMSO-d6): δ 10.41 (1H, s); 8.87 (1H, s); 8.13 (1H, s); 7.57 (1H, brs); 7.28 (1H, s); 7.09 (1H, dd); 7.03 (1H, dt); 6.83–6.78 (2H, m); 6.65 (1H, brd); 3.91 (3H, s); 3.83 (3H, s).

APCI-MS m/z: 354.1 [MH+]

EXAMPLE 56

4-(4-Fluoro-2-methylanilino)-6,7-dimethoxy-3-quinolinecarboxamide $^1$H NMR (DMSO-d6): δ 10.91 (1H, brs); 8.83 (1H, s); 8.22 (1H, brs); 7.61 (1H, brs); 7.26 (1H, s); 7.23–6.93 (5H, m); 7.03 (1H, dt); 3.89 (3H, s); 3.37 (3H, s); 2.28 (3H, s).

APCI-MS m/z: 356.2 [MH+]

EXAMPLE 57

4-[(1-Ethyl-1H-pyrazol-5-yl)amino]-6,7-dimethoxy-3-quinolinecarboxamide

A mixture of 4-chloro-6,7-dimethoxy-3-quinolinecarboxamide (0.046 g, 0.17 mmol), 1-ethyl-5-aminopyrazol (0.030 g, 0.27 mmol) and acetic acid (40 μl) in DMF (0.8 ml) was heated at 100° C. for 7.5 h. The DMF was evaporated under reduced pressure and the residue was dissolved in a mixture of MeCN and water (1:7) containing 0.1% trifluoroacetic acid. Preparative HPLC using a gradient (containing 0.1% trifluoroacetic acid) of 10→40% MeCN in water as eluent gave, after evaporation, the title compound as the trifluoroacetic acid salt. The product was suspended in saturated aqueous NaHCO$_3$ and absorbed on a short SPE column [ISOLUTE™ C18 (EC)] pre-conditioned subsequently with methanol and water. The column was washed extensively with water until the pH of the eluent was neutral. The product was then eluted with methanol, the solvent evaporated and the residue crystallized from ethanol to give the title compound (19 mg, 32%).

$^1$H NMR (DMSO-d6): δ 11.09 (1H, bs); 8.88 (1H, s); 8.34 (1H, bs); 7.71 (1H, bs); 7.42 (1H, d, J 1.4 Hz); 7.27 (1H, s); 6.67 (1H, s); 5.87 (1H, bs); 4.02 (2H, q, J 7.2 Hz); 3.90 (3H, s); 3.46 (3H, s); 3.12 (3H, s); and 1.29 (3H, t, J 7.2 Hz).

APCI-MS m/z: 342.1 [MH+]

EXAMPLE 58

4-(3-Aminocarbonyl-2-methylanilino)-6,7-dimethoxy-3-quinolinecarboxamide

A mixture of 4-chloro-6,7-dimethoxy-3-quinolinecarboxamide (0.046 g, 0.17 mmol), 3-amino 2-metylbenzamide (0.036 g, 0.24 mmol) and acetic acid (40 μl) in DMF (0.8 ml) was heated at 100° C. for 18 h. After cooling the reaction mixture was diluted with water (20 ml) and made alkaline with 1 M NaOH. The precipitate was filtered of, rinsed with water and dried to give the title compound (41 mg, 61%).

$^1$H NMR (DMSO-d6): δ 10.76 (1H, s); 8.90 (1H, s); 8.30 (1H, bs); 7.75 (1H, bs); 7.64 (1H, bs); 7.44 (1H, bs); 7.28 (1H, s); 7.13–7.06 (2H, m); 6.75–6.45 (1H, m); 6.67 (1H, s); 3.90 (3H, s); 3.33 (3H, s) and 2.36 (3H, s).

APCI-MS m/z: 381.1 [MH+]

EXAMPLE 59

6,7-Dimethoxy 4-(2,3-dimethylanilino)-3-quinolinecarboxamide

A mixture of 4-chloro-6,7-dimethoxy-3-quinolinecarboxamide (0.046 g, 0.17 mmol), 2,3-dimethylaniline (20 μl, 0.22 mmol) and acetic acid (40 μl) in DMF (0.8 ml) was heated at 100° C. for 3.5 h. After cooling the reaction mixture was diluted with water (15 ml) and made alkaline with 1 M NaOH. The precipitate was collected by filtration, rinsed with water and dried to give the title compound (48 mg, 79%).

$^1$H NMR (DMSO-d6): δ 10.87 (1H, s); 8.87 (1H, s); 8.26 (1H, bs); 7.58 (1H, bs); 7.24 (1H, s); 7.02–6.96 (1H, m); 6.98 (1H, s); 6.68 (1H, s); 6.66–6.60 (1H, m); 3.88 (3H, s); 3.25 (3H, s); 2.31 (3H, s) and 2.23 (3H, s).

EXAMPLE 60

6,7-Dimethoxy-4-(5,6,7,8-tetrahydro-1-naphtalenylamino)-3-quinolinecarboxamide

A mixture of 4-chloro-6,7-dimethoxy-3-quinolinecarboxamide (0.090 g, 0.34 mmol), 5,6,7,8-tetrahydronaftylamine (0.062 g, 0.42 mmol) and acetic acid (80 μl) in DMF (1.6 ml) was heated at 100° C. for 3.5 h. After cooling the reaction mixture was diluted with water (20 ml) and made alkaline with 1 M NaOH. The precipitate was filtered, rinsed with water and dried to give the title compound (62 mg, 48%).

$^1$H NMR (DMSO-d6): δ 10.66 (1H, s); 8.86 (1H, s); 8.26, 1H, bs); 7.59 (1H, bs); 7.25 (1H, s); 6.98 (1H, t, J 7.7 Hz); 6.86 (1H, d, J 7.4 Hz); 6.70 (1H, s); 6.53 (1H, d, J 7.6 Hz); 3.89 (3H, s); 3.29 (3H, s); 2.76 (1H, bt, J 6 Hz); 2.70 (1H, bt, J 6 Hz); 1.86–1.77 (1H, m) and 1.77–1.69 (1H, m).

APCI-MS m/z: 378.1 [MH+]

EXAMPLE 61

4-(4-Carboxy-2-methylanilino)-6,7-dimethoxy-3-quinolinecarboxamide

A mixture of 4-chloro-6,7-dimethoxy-3-quinolinecarboxamide (0.046 g, 0.17 mmol), 3-amino-2-methylbenzoic acid (0.035 g, 0.23 mmol) and acetic acid (40 μl) in DMSO (0.8 ml) was stirred at 100° C. for 5 h. After cooling the reaction mixture was washed several times with diethyl ether. The oily residue was dissolved in water and made alkaline with 1 M NaOH and then weakly acidified with acetic acid. The mixture was left at 5° C. over night and the resulting precipitate was collected by filtration, washed with water and dried to give the title compound (35 mg, 50%).

$^1$H NMR (DMSO-d6): δ 12.6 (1H, b); 10.74 (1H, s); 8.89 (1H, s); 8.28 (1H, bs); 7.63 (1H, bs); 7.45 (1H, d, J 7.6 Hz); 7.28 (1H, s); 7.13 (1H, t, J 7.8 Hz); 6.84 (1H, t, J 7.9 Hz); 3.90 (3H, s); 3.07 (3H, s) and 2.50 (3H, s).

APCI-MS m/z: 382.1 [MH+]

EXAMPLE 62

4-(1H-Indol-4-ylamino)-6,7-dimethoxy-3-quinolinecarboxamide

A mixture of 4-chloro-6,7-dimethoxy-3-quinolinecarboxamide (0.90 g, 0.34 mmol), 4-aminoindol (0.039 g, 0.23 mmol), sodium acetic (0.020 g, 0.23 mmol) and acetic acid (40 µl) in DMF (0.8 ml) was heated at 100° C. for 4.5 h. After cooling the reaction mixture was diluted with water (20 ml) and made alkaline with 1 M NaOH. The precipitate was isolated by centrifugation, re-suspended in water and centrifuged again. The procedure was repeated twice and the solid material dried to give the title compound (27 mg, 43%).

$^1$H NMR (DMSO-d6): δ 11.20 (1H, s); 11.10 (1H, s); 8.91 (1H, s); 8.27 (1H, bs); 7.60 (1H, bs); 7.27 (1H, m); 7.24 (1H, s); 7.17 (1H, d, J 8.1 Hz); 6.99 (1H, t, J 7.8 Hz); 6.87 (1H, s); 6.50 (1H, d, J 7.5 Hz); 6.21 (1H, m); 3.88 (3H, s) and 3.08 (3H, s).

APCI-MS m/z: 363.1 [MH+]

EXAMPLE 63

4-(3-Chloro-2-methylanilino)-6,7-dimethoxy-3-quinolinecarboxamide

A mixture of 4-chloro-6,7-dimethoxy-3-quinolinecarboxamide (0.046 g, 0.17 mmol), 3-chloro-2-methylaniline (25 µl, 0.21 mmol) and acetic acid (40 µl) in DMF (0.8 ml) was heated at 100° C. for 4.5 h. After cooling the reaction mixture was diluted with water (15 ml) and made alkaline with 1 M NaOH. The precipitate was collected by filtration, rinsed with water and dried to give the title compound (51 mg, 79%).

$^1$H NMR (DMSO-d6): δ 10.65 (1H, s); 8.89 (1H, s); 8.29 (1H, bs); 7.65 (1H, bs); 7.30 (1H, s); 7.17 (1H, d, J 7.8 Hz); 7.01 (1H, t, J 8.0 Hz); 6.71 (1H, s); 6.63 (1H, d, J 7.9 Hz); 3.91 (3H, s); 3.38 (3H, s) and 2.40 (3H, s).

EXAMPLE 64

4-{2-(Aminocarbonyl)anilino]-6,7-dimethoxy-3-quinolinecarboxamide

A mixture of 4-chloro-6,7-dimethoxy-3-quinolinecarboxamide (0.046 g, 0.17 mmol), 2-aminobenzamide (0.029 g, 0.21 mmol) and acetic acid (40 µl) in DMF (0.8 ml) was heated at 100° C. for 6 h. After cooling the reaction mixture was evaporated. The residue was dissolved in a mixture of MeCN and water (1:3) containing 0.1% trifluoroacetic acid and the turbid solution was filtered through a plug of glass wool. Preparative HPLC using a gradient (containing 0.1% trifluoroacetic acid) of 10→40% MeCN in water as eluent gave, after evaporation, the title compound as the trifluoroacetic acid salt. The product was suspended in saturated aqueous NaHCO$_3$ an absorbed on a short SPE column [ISOLUTE™ C18 (EC)] pre-conditioned subsequently with methanol and then water. The column was washed extensively with water until the pH of the eluent was neutral. The product was then eluted with methanol. After evaporation, the residue was crystallized from ethanol to give the title compound (26 mg, 41%).

$^1$H NMR (DMSO-d6): δ 10.87 (1H, s); 8.79 (1H, s); 8.07 (1H, bd, J 7.5 Hz); 7.66 (1H, dd, J 7.7 and 1.2 Hz); 7.47 (1H, bd, J 5.6 Hz); 7.34 (1H, s); 7.20 (1H, dt, J 7.7 and 1.2 Hz); 6.95 (1H, s); 6.92 (1H, d, J 7.4 Hz); 6.52 (1H, d, J 8.1 Hz); 3.93 (3H, s) and 3.50 (3H, s).

APCI-MS m/z: 367.0 [MH+]

EXAMPLE 65

4-(3-Hydroxy-2-methylanilino)-6,7-dimethoxy-3-quinolinecarboxamide

A mixture of 4-chloro-6,7-dimethoxy-3-quinolinecarboxamide (0.046 g, 0.17 mmol), 3-amino-2-methylphenol (0.032 g, 0.26 mmol) and acetic acid (40 µl) in DMF (0.8 ml) was heated at 100° C. for 1.5 h. After cooling, the mixture was diluted with water (15 ml) and made alkaline with saturated NaHCO$_3$. The title compound, which slowly precipitated was filtered off and dried to give 34 mg (55%).

$^1$H NMR (DMSO-d6): δ 10.77 (1H, s); 9.49 (1H, s); 8.86 (1H, s); 8.25 (1H, bs); 7.58 (1H, bs); 7.24 (1H, s); 6.88 (1H, t, J 8.0 Hz); 6.76 (1H, s); 6.61 (1H, d, J 8.0 Hz); 6.23 (1H, d, J 7.9 Hz); 3.89 (3H, s); 3.30 (3H, s) and 2.11 (3H, s).

APCI-MS m/z: 354.1 [MH+]

EXAMPLE 66

6,7-Dimethoxy-4-(3-methoxy-2-methylanilino)-3-quinolinecarboxamide

A mixture of 4-chloro-6,7-dimethoxy-3-quinolinecarboxamide (0.046 g, 0.17 mmol), 3-methoxy-2-methylaniline (0.036 g, 0.26 mmol) and acetic acid (40 µl) in DMF (0.8 ml) was heated at 100° C. for 2.5 h. After cooling, the mixture was diluted with water (15 ml) and made alkaline with saturated NaHCO$_3$. The resulting gummy precipitate was collected and crystallized from methanol-water to give the title compound (45 mg, 70%).

$^1$H NMR (DMSO-d6): δ 10.76 (1H, s); 8.87 (1H, s); 8.26 (1H, bs); 7.60 (1H, bs); 7.25 (1H, s); 7.05 (1H, t, J 8.2 Hz); 6.77 (1H, d, J 8.2 Hz); 6.72 (1H, s); 6.36 (1H, d, J 8.0 Hz); (3.89 (3H, s); 3.81 (3H s); 3.29 (3H, s) and 2.16 (3H, s).

APCI-MS m/z: 368.1 [MH+]

EXAMPLE 67

6,7-Dimethoxy-4-[(1-methyl-1H-indol-4-yl)amino]-3-quinolinecarboxamide

A mixture of 4-chloro-6,7-dimethoxy-3-quinolinecarboxamide (0.028 g, 0.10 mmol), 4-amino-1-methylindol hydrochloride (0.026 g, 0.14 mmol) and sodium acetate (0.013 g, 0.16 mmol) in DMF (0.6 ml) was heated at 100° C. for 8 h. After cooling, the mixture was diluted with water and made alkaline with saturated NaHCO$_3$. The gummy precipitate was collected and crystallized from methanol-water to give the title compound (24 mg, 60%).

$^1$H NMR (DMSO-d6): δ 11.07 (1H, s); 8.91 (1H, s); 8.28 (1H, bs); 7.61 (1H, bs); 7.27 (1H, d, J 3.2 Hz); 7.26 (1H, s); 7.20 (1H, d, J 8.2 Hz); 7.05 (1H, t, J 7.9 Hz); 6.50 (1H, d, J 7.4 Hz); 6.23 (1H, d, J 3.1 Hz); 3.98 (3H, s); 3.79 (3H, s) and 3.12 (3H, s).

APCI-MS m/z: 377.1 [MH+]

EXAMPLE 68

6,7-Dimethoxy-4-[(1-oxo-2,3-dihydro-1H-inden-4-yl)amino]-3-quinolinecarboxamide A mixture of 4-chloro-6,7-dimethoxy-3-quinolinecarboxamide (0.046 g, 0.17 mmol), 4-amino-1-indanone (0.036 g, 0.24 mmol) and acetic acid (40 µl) in DMF (0.6 ml) was heated at 100° C. for 1 h 45 min. After cooling, the mixture was diluted with water and made alkaline with saturated NaHCO$_3$. The precipitate was collected by filtration, washed with water and dried to give title compound (59 mg, 90%).

$^1$H NMR (DMSO-d6): δ 10.60 (1H, s); 8.92 (1H, s); 8.30 (1H, bs); 7.67 (1H, bs); 7.36 (1H, s); 7.32–7.25 (2H, m); 6.89 (1H, dd, J 6.6 and 2.0 Hz); 6.87 (1H, s); 3.94 (3H, s); 3.42 (3H, s); 3.06–2.95 (2H, m) and 2.74–2.67 (2H, m).

APCI-MS m/z: 378.1 [MH+]

EXAMPLE 69

4-[1-Hydroxy-2,3-dihydro-1H-inden-4-yl)amino-6,7-dimethoxy-3-quinolinecarboxamide 6,7-Dimethoxy-4-[(1-oxo-2,3-dihydro-1H-inden-4-yl)amino]-3-quinolinecarboxamide (0.062 g, 16.4 mmol) was dissolved in a mixture of methanol (7 ml), tetrahydrofuran (4 ml) and water (3 ml). Sodium borohydride was added in portions (3×5 mg) and during 5 min. After 20 min the reaction mixture was acidified with acetic acid and then made alkaline with saturated aqueous sodium hydrogencarbonate and evaporated. The residue was partitioned between water and ethyl acetate. The organic phase was washed twice with water and evaporated. The residue was dissolved in methanol and water was added. The title compound, which slowly precipitated, was filtered off and dried to give 40 mg (64%). $^1$H NMR (DMSO-d6): δ 10.68 (1H, s); 8.82 (1H, s); 8.20 (1H, bs); 7.55 (1H, bs); 7.22 (1H, s); 7.07 (1H, t, J 7.5 Hz); 7.04 (1H, t, J 7.4 Hz); 6.75 (1H, s); 6.63 (1H, d, J 7.5 Hz); 5.20 (1H, d, J 5.7 Hz); 5.01 (1H, q, J 6.2 Hz); 3.85 (3H, s); 3.26 (s, moisture signal overlapping); 2.72–2.63 (1H, m); 2.50–2.36 (m, solvent signal overlapping); 2.30–2.20 (1H, m) and 1.76–1.65 (1H, m).

EXAMPLE 70

4-(4-Carboxy-2-methylanilino)-6,7-dimethoxy-3-quinolinecarboxamide

A mixture of 4-chloro-6,7-dimethoxy-3-quinolinecarboxamide (0.046 g, 0.17 mmol), 4-amino-2-methylbenzoic acid (0.036 g, 0.24 mmol) and acetic acid (40 µl) in DMF (0.8 ml) was heated at 100° C. for 12 h. After cooling, the mixture was diluted with water (15 ml) and made alkaline with saturated NaHCO$_3$ and was then weakly acidified with acetic acid. The precipitate was filtered of and suspended in warm methanol. After cooling, the precipitate was filtered off and dried to give the title compound (31 mg, 47%).

$^1$H NMR (DMSO-d6): δ 12.59 (1H, bs); 10.52 (1H, s); 8.93 (1H, s); 8.34 (1H, bs); 7.58 (1H, d J 1.4 Hz); 7.73 (1H, s); 7.60 (1H, dd, J 8.4 and 1.9 Hz); 7.36 (1H, s); 6.75 (1H, s); 6.53 (1H, d J 8.4 Hz); 3.94 (3H, s); 3.42 (3H, s) and 2.41 (3H, s).

APCI-MS m/z: 382.1 [MH+]

EXAMPLE 71

6,7-Dimethoxy-4-(4-methoxycarbonyl-2-methylanilino)-3-quinolinecarboxamide

A mixture of 4-chloro-6,7-dimethoxy-3-quinolinecarboxamide (0.046 g, 0.35 mmol), methyl 4-amino-2-methylbenzoate acid (0.076 g, 0.46 mmol) and acetic acid (100 µl) in DMF (0.8 ml) was heated at 100° C. for 9 h. After cooling, the mixture was combined with two similar reaction mixtures (starting from 92 and 46 mg 4-chloro-6,7-dimethoxy-3-quinolinecarboxamide respectively) and diluted with water. The mixture was made alkaline with saturated NaHCO$_3$ and the gummy precipitate was collected, washed with water and re-crystallized from methanol to give the title compound (130 mg, 47%).

$^1$H NMR (DMSO-d6): δ 10.49 (1H, s); 8.94 (1H, s); 8.35 (1H, bs); 7.88 (1H, d, J 1.4 Hz); 7.62 (1H, dd, J 8.2 and 2.0 Hz); 7.37 (1H, s); 6.53 (1H, d J=8.4 Hz); 3.94 (3H, s); 3.80 (3H, s); 3.43 (3H, s) and 2.43 (3H, s).

APCI-MS m/z: 395.9 [MH+]

EXAMPLE 72

4-(4-Hydroxymethyl-2-methylanilino)-6,7-dimethoxy-3-quinolinecarboxamide 6,7-Dimethoxy-4-(4-methoxycarbonyl-2-methylanilino)-3-quinolinecarboxamide (0.080 g, 0.20 mmol) was dissolved in tetrahydrofuran (25 ml, dried over 4 A molecular sieves). Lithium borohydride (0.15 mg, 6.8 mmol) was added. The mixture was stirred for 24 h and additional lithium borohydride (0.050 g, 2.2 mmol) was added. The reaction mixture was stirred for additional 25 h and then poured into a cooled mixture of water (20 ml) and acetic acid (0.5 ml). Acetic acid (2 ml) was added and the mixture was evaporated under reduced pressure. The residue was suspended in water, filtered and the precipitate was washed with water and re-crystallized from aqueous methanol to give the title compound (32 mg, 43%).

$^1$H NMR (DMSO-d6): δ 11.54 (1H, s); 8.94 (1H, s); 8.46 (1H, bs); 7.86 (1H, s); 7.69 (1H, bs); 7.31 (1H, d J 1.3 Hz); 7.16 (1H, dd, J 8.1 and 1.4 Hz); 7.04 (1H, d, J 8.0 Hz); 6.89 (1H, s); 5.20 (1H, t J5.6 Hz); 4.47 (2H, d, J 5.7 Hz); 3.91 (3H, s); 3.27 (3H, s) and 2.23 (3H, s).

APCI-MS m/z: 368.1 [MH+]

EXAMPLE 73

6,7-Dimethoxy-4-(2-propylanilino)-3-quinolinecarboxamide

A mixture of 4-chloro-6,7-dimethoxy-3-quinolinecarboxamide (0.062 g, 0.23 mmol) 2-propylanilin (0.038 g, 0.28 mmol), 2-butanole (2 ml), DMF (2 ml) and acetic acid (8.2 µl) was heated over night at 100 C. After cooling, the solution was reduced by evaporation. The residue was dissolved in water (3 ml) and treated with aqueous ammonia. The solid product was filtered off washed with water air dried for 0.5 h, washed again with heptane and dried in a vacuum oven at 50 C. to give a yellow-brown solid, 35 mg (41%) of the title compound. APCI-LC/MS m/z 366.1 (MH+): $^1$H NMR (DMSO-d$_6$) δ 10.95 (1H, s); 8.88 (1H, s); 8.28 (1H, br s); 7.62 (1H, br s); 7.29 (1H, m); 7.24 (1H, s);

7.05 (2H, m); 6.68 (1H, m); 6.63 (1H, s); 3.88 (3H, s); 3.21 (3H, s); 2.67 (2H, t); 1.65 (2H, m); 0.93 (3H, t).

The title compounds of examples 74–86 were prepared by a method analogous to that described in Example 73

EXAMPLE 74

4-(2-Isopropylanilino)-6,7-dimethoxy-3-quinolinecarboxamide $^1$H NMR (DMSO-$d_6$) δ 11.07 (1H, s); 8.87 (1H, s); 8.28 (1H, br s); 7.58 (1H, br s); 7.40 (1H, d); 7.23 (1H, s); 7.13 (1H, t); 7.07 (1H, t); 6.68 (1H, d); 6.59 (1H, s); 3.88 (3H, s); 3.35 (1H, m); 3.18 (3H, s); 1.27 (6H, d).

APCI-MS m/z: 366.1 [MH+]

EXAMPLE 75

4-[2-(sec-Butyl)anilino]-6,7-dimethoxy-3-quinolinecarboxamide $^1$H NMR (DMSO-$d_6$): δ 11.08 (1H, s); 8.87 (1H, s); 8.28 (1H, br s); 7.59 (1H, br s); 7.34 (1H, d); 7.22 (1H, s); 7.13 (1H, t); 7.07 (1H, t); 6.68 (1H, d); 6.61 (1H, s); 3.86 (3H, s); 3.17 (3H, s); 3.13 (1H, m); 1.65 (2H, m); 1.21 (3H, d); 0.80 (3H, t).

APCI-MS m/z: 380.2 [MH+]

EXAMPLE 76

6,7-Dimethoxy-4-[3-(methoxymethyl)-2-methylanilino]-3-quinolinecarboxamide $^1$H NMR (DMSO-$d_6$) δ 10.82 (1H, s); 8.86 (1H, s); 8.25 (1H, br s); 7.58 (1H, br s); 7.22 (1H, s); 7.08 (2H, m); 6.71 (1H, d); 6.64 (1H, s); 4.45 (2H, s); 3.86 (3H, s); 3.22 (3H, s); 2.25 (3H, s).

APCI-MS m/z: 382.1 [MH+]

EXAMPLE 77

4-[3-(iso-Butoxymethyl)-2-methylanilino]-6,7-dimethoxy-3-quinolinecarboxamide $^1$H NMR (DMSO-$d_6$) δ 10.83 (1H, s); 8.83 (1H, s); 8.23 (1H, br s); 7.58 (1H, br s); 7.22 (1H, s); 7.08 (2H, m); 6.72 (1H, d); 6.62 (1H, s); 4.48 (2H, s); 3.86 (3H, s); 3.22 (3H, s); 3.19 (2H, d); 2.25 (3H, s); 1.80 (1H, m); 0.84 (6H, d).

APCI-MS m/z: 424.1 [MH+]

EXAMPLE 78

4-[3-(cyanomethyl)-2-methylanilino]-6,7-dimethoxy-3-quinoline carboxamide $^1$H NMR (DMSO-$d_6$) δ 10.76 (1H, s); 8.86 (1H, s); 8.25 (1H, br s); 7.60 (1H, br s); 7.24 (1H, s); 7.12 (2H, m); 6.71 (1H, d); 6.61 (1H, s); 4.07 (2H, s); 3.87 (3H, s); 3.22 (3H, s); 2.30 (3H, s).

APCI-LC/MS m/z 377.1 [MH+]

EXAMPLE 79

4-{3-[(Ethylamino)methyl]-2-methylanilino}-6,7-dimethoxy-3-quinolinecarboxamide

The title compoundswas prepared starting from tert-butyl 3-amino-2-methylbenzyl(ethyl)carbamate, deprotection using TFA gives the title compound.

$^1$H NMR (CDCl$_3$) δ 10.68 (1H, s); 8.75 (1H, s); 7.23 (1H, s); 7.13 (1H, d); 7.05 (1H, t); 6.83 (1H, d); 6.72 (1H, s); 6.25 (2H, br s); 3.95 (3H, s); 3.82 (2H, s); 3.31 (3H, s); 2.73 (2H, q); 2.35 (3H, s); 0.64 (3H, t).

APCI-MS m/z: 395.1 [MH+]

EXAMPLE 80

4-{3-[2-(Ethylamino)-2-oxoethyl]-2-methylanilino}-6,7-dimethoxy-3-quinolinecarboxamide $^1$H NMR (DMSO-$d_6$) δ 10.86 (1H, s); 8.85 (1H, s); 8.23 (1H, br s); 7.94 (1H, m); 7.56 (1H, br s); 7.21 (1H, s): 7.01 (1H, d); 6.66 (1H, m); 6.62 (1H, s); 3.86 (3H, s); 3.49 (2H, s); 3.21 (3H, s); 3.05 (2H, m); 2.25 (3H, s); 1.00 (3H, t).

APCI-MS m/z: 423.3 [MH+]

EXAMPLE 81

Ethyl 2-(3-{[3-(aminocarbonyl)-6,7-dimethoxy-4-quinolinyl]amino}-2-methylphenyl)acetate $^1$H NMR (DMSO-$d_6$) δ 10.87 (1H, s); 8.86 (1H, s); 8.26 (1H, br s); 7.56 (1H, br s); 7.22 (1H, s); 7.04 (2H, m); 6.72 (1H, m); 6.16 (1H, s); 4.06 (2H, q); 3.86 (3H, s); 3.76 (2H, s); 3.23 (3H, s); 2.20 (3H, s); 1.15 (3H, t).

APCI-MS m/z: 424.1 [MH+]

EXAMPLE 82

4-[3-(1-Amino-2-oxoethyl)-2-methylanilino[-6,7-dimethoxy-3-quinolinecarboxamide $^1$H NMR (DMSO-$d_6$) δ 10.83 (1H, s); 8.83 (1H, s); 8.24 (1H, br s); 7.56 (1H, br s); 7.38 (1H, br s); 7.21 (1H, s); 7.08 (2H, m); 6.89 (1H, br s); 6.66 (1H, m); 6.62 (1H, s); 3.86 (3H, s); 3.50 (2H, s); 3.22 (3H, s); 2.26 (3H, s).

APCI-MS m/z: 395.1 [MH+]

EXAMPLE 83

4-[3-(2-Hydroxyethyl)-2-methylanilino]-6,7-dimethoxy-3-quinolinecarboxamide $^1$H NMR (DMSO-$d_6$) δ 10.82 (1H, s); 8.82 (1H, s); 8.23 (1H, br s); 7.56 (1H, br s); 7.22 (1H, s); 7.01 (2H, m); 6.62 (2H, m); 4.66 (1H, t); 3.86 (3H, s); 3.55 (2H, q); 3.21 (3H, s); 2.82 (2H, t); 2.27 (3H, s).

APCI-MS m/z: 382.1 [MH+]

EXAMPLE 84

4-(3-{2-[(2-Hydroxyethyl)amino]-2-oxoethyl}-2-methylanilino)-6,7-dimethoxy3-quinolinecarboxamide $^1$H NMR (DMSO-d$_6$) δ 10.83 (1H, s); 8.82 (1H, s); 8.25 (1H, br s); 7.95 (1H, m); 7.58 (1H, br s); 7.21 (1H, s); 7.03 (2H, m); 6.68 (1H, m); 6.62 (1H, s); 4.65 (1H, t); 3.86 (3H, s); 3.54 (2H, s); 3.39 (2H, m); 3.23 (3H, s); 3.12 (2H, m); 2.26 (3H, s).

APCI-MS m/z: 439.1 [MH+]

EXAMPLE 85

Tert-Butyl 3-{[3-(aminocarbonyl)-6,7-dimethoxy-4-quinolinyl]amino}-2-methylbenzylcarbamate $^1$H NMR (DMSO-d6) δ 10.83 (1H, s); 8.84 (1H, s); 8.22 (1H, br s); 7.55 (1H, br s); 7.32 (1H, m); 7.22 (1H, s); 7.08 (2H, m): 6.66 (1H, d); 6.60 (1H, s); 4.15 (2H, d); 3.85 (3H, s); 3.21 (3H, s) 2.25 (3H, s); 1.39 (9H, s).

APCI-MS m/z: 467.2 [MH+]

EXAMPLE 86

4-[3-(Aminomethyl)-2-methylanilino]-6,7-dimethoxy-3-quinolinecarboxamide

Tert-butyl 3-{[3-(aminocarbonyl)-6,7-dimethoxy-4-quinolinyl]amino}-2-methylbenzyl carbamate (0.12 mg, 0.25 mmol) was dissolved in CH$_2$Cl$_2$ (5 ml), cooled on ice and TFA (3 ml) was added. After 2 h stirring at room temperature the mixture was evaporated to give an oil, which was dissolved in CH$_2$Cl$_2$/aq.Na$_2$CO$_3$ solution. The aqueous phase was extracted with CH$_2$Cl$_2$ (×6). The extracts were washed with brine, dried (Na$_2$SO$_4$), and evaporated. The residue was purified by chromatography (CH$_2$Cl$_2$/MeOH/NH$_3$) to give the title compound 54 mg, (59%) as a white powder.

$^1$H NMR (CDCl$_3$) δ 10.83 (1H, s); 8.82 (1H, s); 8.11 (1H, br s); 7.55 (1H, br s); 7.22 (1H, s); 7.16 (1H, d); 7.05 (1H, m); 6.65 (2H, m); 3.86 (3H, s); 3.75 (2H, s); 3.22 (3H, s); 2.27 (3H, s).

APCI-MS m/z: 353.1 [MH+]

Intermediates used as starting meterials in examples 87–179

Etyl 7-methoxy-4-chloro-3-quinolinecarboxamide.

The title compound were prepared essentially as described by Burke. et al. *J. Med. Chem,* 36(1993)425–432

7-Methoxy-4-chloro-3-quinolinecarboxamide $^1$H NMR (DMSO-d6): δ 8.80 (1H, s); 8.19 (1H, s); 8.15 (1H, br s); 7.90 (1H, br s); 7.50 (1H, d); 7.46 (1H, dd); 3.96 (3H, s).

Ethyl 4-chloro-3-quinolinecarboxamide

The title compound were prepared essentially as described by Burke. et al. *J. Med. Chem,* 36(1993)425–432.

4-Chloro-3-quinolinecarboxamide $^1$H NMR (DMSO-d6): δ 8.8 (1H, s); 8.30 (1H, d); 8.19 (1H, br s); 8.13 (1H, d); 7.96 (1H, br s); 7.93 (1H, t); 7.83 (1H, t).

Ethyl 6,7-dichloro-4-chloro-3-quinolinecarboxamide

The title compound were prepared essentially as described by Burke. et al. *J. Med. Chem,* 36(1993)425–432.

6,7-Dichloro-4-chloro-3-quinolinecarboxamide $^1$H NMR (DMSO-d6): δ 8.94 (1H, s); 8.47 (2H, d); 8.27 (1H, br s); 8.06 (1H, br s).

Etyl 6-methoxy-4-chloro-3-quinolinecarboxamide.

The title compound were prepared essentially as described by Burke. et al. *J. Med. Chem,* 36(1993)425–432.

6-Methoxy-4-chloro-3-quinolinecarboxamide $^1$H NMR (DMSO-d6): δ 8.70 (1H, s); 8.17 (1H, br s); 8.04 (1H, d); 7.92 (1H, br s); 7.56 (1H, dd); 7.52 (1H, d); 3.97 (3H, s).

EXAMPLE 87

4-(4-Fluoro-2-methylanilino)-6-methoxy-3-quinolinecarboxamide

A mixture of 4-fluoro-2-methylaniline (0.025 mmol), 6-methoxy-4-chloro-3-quinolinecarboxamide (0.025 mmol), 50 μl 20% Acetic acid/Ethanol and 250 μl ethanol was refluxed for four hours. After cooling to room temperature the solvent was removed in vacuu.

APCI-MS m/z: 326 [MH+]

the title compounds of example 88–179 were prepared by a method analogous to that described in Example 87.

EXAMPLE 88

4-(4-Bromo-2-methylanilino)-6-methoxy-3-quinolinecarboxamide

APCI-MS m/z: 388 [MH+]

EXAMPLE 89

4-(4-Chloro-2-methylanilino)-6-methoxy-3-quinolinecarboxamide

APCI-MS m/z: 342 [MH+]

EXAMPLE 90

4-(2,4-Dimethylanilino)-6-methoxy-3-quinolinecarboxamide

APCI-MS m/z: 322 [MH+]

EXAMPLE 91

6-Methoxy-4-(4-methoxy-2-methylanilino)-3-quinolinecarboxamide

APCI-MS m/z: 338 [MH+]

EXAMPLE 92

4-(4-Hydroxy-2-methylanilino)-6-methoxy-3-quinolinecarboxamide

APCI-MS m/z: 324 [MH+]

EXAMPLE 93

4-(2-Bromoanilino)-6-methoxy-3-quinolinecarboxamide

APCI-MS m/z: 374 [MH+]

EXAMPLE 94

4-(2,4-Dimethoxyanilino)-6-methoxy-3-quinolinecarboxamide

APCI-MS m/z: 354 [MH+]

EXAMPLE 95

6-Methoxy-4-(2-methoxyanilino)-3-quinolinecarboxamide

APCI-MS m/z: 324 [MH+]

EXAMPLE 96

4-(2-Ethoxyanilino)-6-methoxy-3-quinolinecarboxamide

APCI-MS m/z: 338 [MH+]

EXAMPLE 97

4-(2-Ethylanilino)-6-methoxy-3-quinolinecarboxamide

APCI-MS m/z: 322 [MH+]

EXAMPLE 98

6-Methoxy-4-(2-toluidino)-3-quinolinecarboxamide

APCI-MS m/z: 308 [MH+]

EXAMPLE 99

6-Methoxy-4-[2-(methylsulfanyl)anilino]-3-quinolinecarboxamide

APCI-MS m/z: 340 [MH+]

EXAMPLE 100

4-(4-Bromo-2-methylanilino)-6,7-dimethoxy-3-quinolinecarboxamide

APCI-MS m/z: 417 [MH+]

EXAMPLE 101

4-(4-Chloro-2-methylanilino)-6,7-dimethoxy-3-quinolinecarboxamide

APCI-MS m/z: 372 [MH+]

EXAMPLE 102

4-(2,4-Dimethylanilino)-6,7-dimethoxy-3-quinolinecarboxamide

APCI-MS m/z: 352 [MH+]

EXAMPLE 103

6,7-Dimethoxy-4-(4-methoxy-2-methylanilino)-3-quinolinecarboxamide

APCI-MS m/z: 368 [MH+]

EXAMPLE 104

4-(2-Bromo-4-methylanilino)-6,7-dimethoxy-3-quinolinecarboxamide

APCI-MS m/z: 417 [MH+]

EXAMPLE 105

4-(2-Bromo-4-fluoroanilino)-6,7-dimethoxy-3-quinolinecarboxamide

APCI-MS m/z: 421 [MH+]

EXAMPLE 106

4-(2,4-Dimethoxyanilino)-6,7-dimethoxy-3-quinolinecarboxamide

APCI-MS m/z: 384 [MH+]

EXAMPLE 107

4-(4-Fluoro-2-methylanilino)-7-methoxy-3-quinolinecarboxamide

APCI-MS m/z: 326 [MH+]

EXAMPLE 108

4-(4-Bromo-2-methylanilino)-7-methoxy-3-quinolinecarboxamide

APCI-MS m/z: 388 [MH+]

EXAMPLE 109

4-(4-Chloro-2-methylanilino)-7-methoxy-3-quinolinecarboxamide

APCI-MS m/z: 342 [MH+]

EXAMPLE 110

4-(2,4-Dimethylanilino)-7-methoxy-3-quinolinecarboxamide

APCI-MS m/z: 322 [MH+]

EXAMPLE 111

7-Methoxy-4-(4-methoxy-2-methylanilino)-3-quinolinecarboxamide

APCI-MS m/z: 338 [MH+]

EXAMPLE 112

4-(4-Hydroxy-2-methylanilino)-7-methoxy-3-quinolinecarboxamide

APCI-MS m/z: 324 [MH+]

EXAMPLE 113

4-(2-Bromoanilino)-7-methoxy-3-quinolinecarboxamide

APCI-MS m/z: 374 [MH+]

EXAMPLE 114

4-(2-Bromo-4-methylanilino)-7-methoxy-3-quinolinecarboxamide

APCI-MS m/z: 388 [MH+]

EXAMPLE 115

4-(2-Bromo-4-fluoroanilino)-7-methoxy-3-quinolinecarboxamide

APCI-MS m/z: 390 [MH+]

EXAMPLE 116

4-(2,4-Dimethoxyanilino)-7-methoxy-3-quinolinecarboxamide

APCI-MS m/z: 354 [MH+]

EXAMPLE 117

6,7-Dichloro-4-(4-methoxy-2-methylanilino)-3-quinolinecarboxamide

APCI-MS m/z: 376 [MH+]

EXAMPLE 118

6,7-Dichloro-4-(2,4-dimethoxyanilino)-3-quinolinecarboxamide

APCI-MS m/z: 392 [MH+]

EXAMPLE 119

4-(2-Ethylanilino)-3-quinolinecarboxamide

APCI-MS m/z: 292 [MH+]

EXAMPLE 120

4-(2-Toluidino)-3-quinolinecarboxamide

APCI-MS m/z: 278 [MH+]

EXAMPLE 121

4-[2-(Methylsulfanyl)anilino]-3-quinolinecarboxamide

APCI-MS m/z: 310 [MH+]

EXAMPLE 122

4-(2-Ethoxyanilino)-6,7-dimethoxy-3-quinolinecarboxamide

APCI-MS m/z: 368 [MH+]

EXAMPLE 123

4-[2-(Hydroxymethyl)anilino]-6,7-dimethoxy-3-quinolinecarboxamide

APCI-MS m/z: 354 [MH+]

EXAMPLE 124

4-(2-Ethylanilino)-6,7-dimethoxy-3-quinolinecarboxamide

APCI LC/Ms m/z: 352 [MH+]

EXAMPLE 125

6,7-Dimethoxy-4-(2-toluidino)-3-quinolinecarboxamide

APCI-MS m/z: 338 [MH+]

EXAMPLE 126

6,7-Dimethoxy-4-[2-(methylsulfanyl)anilino]-3-quinolinecarboxamide

APCI-MS m/z: 370 [MH+]

EXAMPLE 127

4-(2,4-Dibromoanilino)-6,7-dimethoxy-3-quinolinecarboxamide

APCI-MS m/z 481 [MH+]

EXAMPLE 128

7-Methoxy-4-(2-methoxyanilino)-3-quinolinecarboxamide

APCI-MS m/z: 324 [MH+]

EXAMPLE 129

4-(2-Ethoxyanilino)-7-methoxy-3-quinolinecarboxamide

APCI-MS m/z: 328 [MH+]

EXAMPLE 130

4-[2-(Aminocarbonyl)anilino[-7-methoxy-3-quinolinecarboxamide

APCI-MS m/z: 337 [MH+]

EXAMPLE 131

4-(2-Ethylanilino)-7-methoxy-3-quinolinecarboxamide

APCI-MS m/z: 322 [MH+]

EXAMPLE 132

7-Methoxy-4-(2-toluidino)-3-quinolinecarboxamide

APCI-MS m/z: 308 [MH+]

EXAMPLE 133

7-Methoxy-4-[2-(methylsulfanyl)anilino]-3-quinolinecarboxamide

APCI-MS m/z: 340 [MH+]

EXAMPLE 134

6,7-Dichloro-4-(2-methoxyanilino)-3-quinolinecarboxamide

APCI-MS m/z: 361 [MH+]

EXAMPLE 135

6,7-Dichloro-4-(2-ethylanilino)-3-quinolinecarboxamide

APCI-MS m/z: 360 [MH+]

EXAMPLE 136

6,7-Dichloro-4-[2-(methylsulfanyl)anilino]-3-quinolinecarboxamide

APCI-MS m/z: 378 [MH+]

EXAMPLE 137

4-(2,5-Dimethylanilino)-6,7-dimethoxy-3-quinolinecarboxamide

APCI-MS m/z: 352 [MH+]

EXAMPLE 138

4-(5-Fluoro-2-methylanilino)-6,7-dimethoxy-3-quinolinecarboxamide

APCI-MS m/z: 356 [MH+]

EXAMPLE 139

4-(5-Chloro-2-methylanilino)-6,7-dimethoxy-3-quinolinecarboxamide

APCI-MS m/z: 372 [MH+]

EXAMPLE 140

4-(3-Fluoro-2-methylanilino)-6,7-dimethoxy-3-quinolinecarboxamide

APCI-MS m/z: 356 [MH+]

EXAMPLE 141

4-(4-Hydroxy-2,5-dimethylanilino)-6,7-dimethoxy-3-quinolinecarboxamide

APCI-MS m/z: 368 [MH+]

EXAMPLE 142

4-(2-Hydroxy-4-methylanilino)-6,7-dimethoxy-3-quinolinecarboxamide

APCI-MS m/z: 354 [MH+]

EXAMPLE 143

4-Anilino-6,7-dimethoxy-3-quinolinecarboxamide

APCI-MS m/z: 324 [MH+]

EXAMPLE 144

4-(4-Chloro-2-fluoroanilino)-6,7-dimethoxy-3-quinolinecarboxamide

APCI-MS m/z: 375 [MH+]

EXAMPLE 145

4-(2-Fluoroanilino)-6,7-dimethoxy-3-quinolinecarboxamide

APCI-MS m/z: 341 [MH+]

EXAMPLE 146

4-(2,6-Difluoroanilino)-6,7-dimethoxy-3-quinolinecarboxamide

APCI-MS m/z: 359 [MH+]

EXAMPLE 147

4-(3-Bromoanilino)-6,7-dimethoxy-3-quinolinecarboxamide

APCI-MS m/z: 401, 403 [MH+]

EXAMPLE 148

4-(3-Fluoroanilino)-6,7-dimethoxy-3-quinolinecarboxamide

APCI-MS m/z: 341 [MH+]

EXAMPLE 149

6,7-Dimethoxy-4-(4-methoxyanilino)-3-quinolinecarboxamide

APCI-MS m/z: 337 [MH+]

EXAMPLE 150

4-(3-Chloroanilino)-6,7-dimethoxy-3-quinolinecarboxamide

APCI-MS m/z: 357 [MH+]

EXAMPLE 151

4-(2-Chloroanilino)-6,7-dimethoxy-3-quinolinecarboxamide

APCI-MS m/z: 357 [MH+]

EXAMPLE 152

4-[3-(Acetylamino)anilino]-6,7-dimethoxy-3-quinolinecarboxamide

APCI-MS m/z: 380 [MH+]

EXAMPLE 153

4-(2,5-Difluoroanilino)-6,7-dimethoxy-3-quinolinecarboxamide

APCI-MS m/z: 359 [MH+]

EXAMPLE 154

4-(1H-Indol-5-ylamino)-6,7-dimethoxy-3-quinolinecarboxamide

APCI-MS m/z: 363 [MH+]

EXAMPLE 155

4-(1H-Indazol-5-ylamino)-6,7-dimethoxy-3-quinolinecarboxamide

APCI-MS m/z: 364 [MH+]

EXAMPLE 156

4-(1H-Indazol-6-ylamino)-6,7-dimethoxy-3-quinolinecarboxamide

APCI-MS m/z: 364 [MH+]

EXAMPLE 157

4-(2,4-Difluoroanilino)-6,7-dimethoxy-3-quinolinecarboxamide

APCI-MS m/z: 359 [MH+]

EXAMPLE 158

4-(2-Fluoro-4-methylanilino)-6,7-dimethoxy-3-quinolinecarboxamide

APCI-MS m/z: 356 [MH+]

EXAMPLE 159

4-(2,4-Dichloroanilino)-6,7-dimethoxy-3-quinolinecarboxamide

APCI-MS m/z: 391, 393 [MH+]

EXAMPLE 160

4-(2,5-Dichloroanilino)-6,7-dimethoxy-3-quinolinecarboxamide

APCI-MS m/z: 391, 393 [MH+]

EXAMPLE 161

4-[2-(2-Hydroxyethyl)anilino]-6,7-dimethoxy-3-quinolinecarboxamide

APCI-MS m/z: 368 [MH+]

EXAMPLE 162

4-(3-Chloro-4-fluoroanilino)-6,7-dimethoxy-3-quinolinecarboxamide

APCI-MS m/z: 375 [MH+]

EXAMPLE 163

6,7-Dimethoxy-4-[3-(methylsulfanyl)anilino]-3-quinolinecarboxamide

APCI-MS m/z: 370 [MH+]

EXAMPLE 164

6,7-Dimethoxy-4-(2-methoxy-5-methylanilino)-3-quinolinecarboxamide

APCI-MS m/z: 368 [MH+]

EXAMPLE 165

4-[4-(Dimethylamino)anilino]-6,7-dimethoxy-3-quinolinecarboxamide

APCI-MS m/z: 367 [MH+]

EXAMPLE 166

6,7-Dimethoxy-4-[4-(methylsulfanyl)anilino]-3-quinolinecarboxamide

APCI-MS m/z: 370 [MH+]

EXAMPLE 167

4-[4-(2-Hydroxyethyl)anilino]-6,7-dimethoxy-3-quinolinecarboxamide

APCI-MS m/z: 368 [MH+]

EXAMPLE 168

4-(3-Hydroxy-4-methoxyanilino)-6,7-dimethoxy-3-quinolinecarboxamide

APCI-MS m/z: 370 [MH+]

EXAMPLE 169

4-(2,3-Dichloroanilino)-6,7-dimethoxy-3-quinolinecarboxamide

APCI-MS m/z: 391 [MH+]

EXAMPLE 170

6,7-Dimethoxy-4-(2,3,4-trifluoroanilino)-3-quinolinecarboxamide

APCI-MS m/z: 378 [MH+]

EXAMPLE 171

6,7-Dimethoxy-4-(3-toluidino)-3-quinolinecarboxamide

APCI-MS m/z: 338 [MH+]

EXAMPLE 172

4-(2-Hydroxy-4-methylanilino)-6,7-dimethoxy-3-quinolinecarboxamide

APCI-MS m/z: 354 [MH+]

EXAMPLE 173

4-(2-Fluoro-4-hydroxyanilino)-6,7-dimethoxy-3-quinolinecarboxamide

APCI-MS m/z: 358 [MH+]

EXAMPLE 174

4-[2-(Hydroxymethyl)-4-methylanilino]-6,7-dimethoxy-3-quinolinecarboxamide

APCI-MS m/z: 368 [MH+]

EXAMPLE 175

4-(2-Chloro-4-fluoroanilino)-6,7-dimethoxy-3-quinolinecarboxamide

APCI-MS m/z: 375 [MH+]

EXAMPLE 176

4-(2-Fluoro-5-methylanilino)-6,7-dimethoxy-3-quinolinecarboxamide

APCI-MS m/z: 356 [MH+]

EXAMPLE 177

4-[(2-Cyanophenyl)amino]-6,7-dimethoxyquinoline-3-carboxamide

APCI-MS m/z: 349 [MH+]

EXAMPLE 178

4-[(2,5-Difluorophenyl)amino]-6,7-dimethoxyquinoline-3-carboxamide

APCI-MS m/z: 360 [MH+]

EXAMPLE 179

4-(1H-Indol-5-ylamino)-6,7-dimethoxyquinoline-3-carboxamide

APCI-MS m/z: 363 [MH+]

EXAMPLE 180

6,7-Dichloro-4-(2-methylanilino)-3-quinolinecarboxamide

A mixture of Ethyl-6,7-dichloro-4-(2-methylanilino)-3-quinolinecarboxylate (0.050 g, mmol) and NH$_4$Cl was heated in a pressure vessel with NH$_3$-saturated methanol for five days. The mixture was evaporated and the residue was recrystallized from EtOH.

$^1$H NMR (DMSO-d6): δ 10.9 (1H, s); 9.0 (1H, s); 8.3 (1H, br s); 8.1 (1H, s); 7.7 (1H, br s); 7.6 (1H, s); 7.6 (1H, dd); 7.2 (2H, m); 6.6 (1H, dd); 2.27 (3H, s).

EXAMPLE 181

4-(2,3-Dihydro-1H-inden-1-ylamino)-6,7-dimethoxy-3-quinoline carboxamide

A mixture of 4-chloro-6,7-dimethoxy-3-quinolinecarboxamide (0.066 g, 0.25 mmol), 1-aminoindan (0.66 mg, 0.50 mmol), 2-butanole (2 ml), DMF (2 ml) was heated for 48 h at 100° C. After cooling, the solution was reduced by evaporation. The residue was dissolved in water (3 ml) and treated with aqueous ammonia. The solid product was fitered off washed with water air dried for 0.5 h, washed again with heptane and dried. The residue was purified by chromatography on silica ($CH_2Cl_2$/MeOH) to give 63 mg, (70%) of the title compound as a white solid.

$^1$H NMR (DMSO-$d_6$): δ 8.74 (1H, d); 8.63 (1H, s); 8.05 (1H, br s); 7.55 (1H, s); 7.35 (1H, br s); 7.30–7.14 (5H, m); 5.46 (1H, q); 3.89 (3H, s); 3.83 (3H, s); 2.99–2.91 (1H, m); 2.88–2.76 (1H, m); 2.62–2.52 (1H, m); 1.02–0.91 (1H, m).

APCI-MS m/z: 364.1 [MH+]

the title compounds of examples 182–183 were prepared by a method analogous to that described in Example 181.

EXAMPLE 182

6,7-Dimethoxy-4-{[2-(trifluoromethyl)benzyl]amino}-3-quinoline carboxamide $^1$H NMR (DMSO-$d_6$): δ 8.91 (1H, t); 8.59 (1H, s); 7.98 (1H, br s); 7.75 (2H, m); 7.68 (1H, t); 7.51 (1H, t); 7.34 (1H, br s); 7.25 (1H, s); 7.21 (1H, s); 4.91 (2H, d); 3.88 (3H, s); 3.51 (3H, s).

APCI-MS m/z: 406.1 [MH+]

EXAMPLE 183

6,7-Dimethoxy-4-[(1-phenylethyl)amino]-3-quinolinecarboxamide $^1$H NMR (DMSO-$d_6$): δ 9.40 (1H, d); 8.66 (1H, s); 8.06 (1H, br s); 7.43–7.35 (2H, m); 7.30 (2H, t); 7.18–7.22 (2H, m); 7.14 (1H, s); 5.18 (1H, m); 3.83 (3H, s); 3.45 (3H, s); 1.52 (3H, d).

APCI-MS m/z: 352.1 [MH+]

EXAMPLE 184

4-(3-Hydroxymethyl-2-methylanilino)-3-quinolinecarboxamide a) Diethyl 2-[1,3-benzodioxol-5-ylamino)methylene]malonate Diethyl 2-(ethoxymethylene)malonate (4.1 ml, 20.3 mmol) 3,4-methylenedioxyaniline (2.77 g, 20.2 mmol) was stirred under nitrogen at 120° C. for 2.5 h. The reaction mixture was cooled and ethanol was added. The precipitate was collected by filtration and re-crystallized from ethanol to give the title compound (3.52 g, 56%)

$^1$H NMR (DMSO-d6): δ 10.67 (1H, d, J 13.9 Hz); 8.28 (1H, d, J 13.9 Hz); 7.12 (1H, d, J 2.2 Hz); 6.91 (1H, d, J 8.3 Hz); 6.81 (1H, dd, J 8.4 and 2.3 Hz); 6.04 (2H, s); 4.19 (2H, q, J 7.1 Hz); 4.10 (2H, q, J 7.1 Hz); 1.25 (3H, t, J 7.1 Hz); and 1.23 (3H, t, J 7.2 Hz).

b) Ethyl 4-chloro-6,7-methylenedioxy-3-quinolinecarboxamide

Diethyl 2-[1,3-benzodioxol-5-ylamino)methylene]malonate (3.25 g, 11.6 mmol) was dissolved in $POCl_3$ (60 ml) and heated at reflux for 4.5 h, cooled and co-evaporated twice with toluene. The residue was suspended in ice-cold saturated aqueous $NaHCO_3$ and the precipitate was collected by filtration, rinsed with wate and dried to give the title compound (3.01 g, 95%).

$^1$H NMR (DMSO-d6): δ 8.92 (1H, s); 7.64 (1H, s); 7.49 (1H, s); 6.33 (2H, s); 4.40 (2H, q, J 7.1 Hz) and 1.36 (3H, t, J 7.1 Hz).

APCI-MS m/z: 279.9 [MH+]

c) 4-Chloro-6,7-methylenedioxy-3-quinolinecarboxylic acid

Ethyl 4-chloro-6,7-methylenedioxy-3-quinolinecarboxylate (1.54 g, 5.5 mmol) was suspended in a mixture of ethanol (25 ml), THF (5 ml) and aqueous 2 M NaOH (25 ml) and stirred at ambient temperature for 2 h. The reaction mixture was neutralized with 1 M aqueous HCl and the organic solvents were evaporated under reduced pressure. After acidification to pH 2–3 with 1 M HCl the resulting precipitate was isolated by centrifugation. The precipitate was re-suspended in water and centrifuged again. The procedure was repeated twice to give, after drying, the title compound (1.25 g, 90%)

$^1$H NMR (DMSO-d6): δ 13.71 (1H, bs); 8.93 (1H, s); 7.63 (1H, s); 7.47 (1H, s) and 6.32 (2H, s).

d) 3-Chloro-6,7-methylenedioxy-3-quinolinecarboxamide

4-Chloro-6,7-methylenedioxy-3-quinolinecarboxylic acid (0.68 g, 2.7 mmol) was suspended in thionyl chloride (30 ml) and the mixture was heated to reflux for 1 h and then co-evaporated with toluene. The residue was suspended in ice-cold acetone (25 ml) and treated with ice-cold saturated aqueous ammonia (28%, 2 ml) in portions at 0° C. The reaction mixture was stirred at 0° C. for 2 min and then filtered. The solid material was washed with water and dried to give the title compound (501 mg, 74%).

$^1$H NMR (DMSO-d6): δ 8.63 (1H, s); 8.10 (1H, bs); 7.84 (1H, s); 7.56 (1H, s); 7.46 (1H, s) and 6.30 (2H, s).

e) 4-(3-Hydroxymethyl-2-methylanilino)-3-quinolinecarboxamide

A mixture of 3-Chloro-6,7-methylenedioxy-3-quinolinecarboxamide (106 mg, 0.42 mmol); 3-amino-2-methylbenzylalcohol (72 mg, 0.52 mmol) and acetic acid (100 μL) in DMF (2 ml) was heated at 100° C. for 6 h. After cooling, the mixture was diluted with water (20 ml) and washed twice with ethyl acetate. The aqueous phase was made alkaline with 1 M NaOH and the resulting precipitate was collected by filtration, washed with water and dried to give the title compound (113 mg, 75%).

$^1$H NMR (DMSO-d6): δ 10.47 (1H, s); 8.86 (1H, s); 8.30 (1H, s); 7.64 (1H, s); 7.26 (1H, s); 7.13 (1H, d, J 7.3 Hz); 7.00 (1H, t, J 7.7 Hz); 6.66 (1H, s); 6.49 (1H, d, J 7.8 Hz); 6.11 (2H, s); 5.14 (1H, bs); 4.56 (2H, s) and 2.28 (3H, s).

APCI-MS m/z: 352.1 [MH+]

EXAMPLE 185

9-(3-Hydroxymethyl-2-methylanilino)-2,3-dihydro[1,4]dioxino[2,3g]quinoline-8-carboxamide a) Ethyl 9-chloro-2,3-dihydro[1,4]dioxino[2,3g]quinoline-8-carboxylate Diethyl 2-(ethoxymethylene)malonate (4.1 ml, 20.3 mmol) and 2,3-dihydro-1,4-benzodioxin-6-amine (2.48 ml, 20.2 mmol) was stirred under nitrogen at 120° C. for 4 h and the reaction mixture was then evaporated under reduced pressure. The crude diethyl 2-[2,3-dihydro-1,4-benzodioxin-6-ylamino)methylene]malonate was dissolved in $POCl_3$ and heated at reflux for 5 h and the mixture was then co-evaporated with toluene. The residue was dissolved in methylene chloride and washed with saturated aqueous $NaHCO_3$ and water, dried ($Na_2SO_4$), filtered and evaporated. The residue was crystallized from methanol-water to give 3.5 g of crude product. Re-crystallization from methanol-water and finally from methanol gave the title compound (1.14 g, 19%).

$^1$H NMR (DMSO-d6): δ 8.93 (1H, s); 7.65 (1H, s); 7.51 (1H, s); 4.49–4.42 (4H, m); 4.40 (2H, q, J 7.1 Hz) and 1.36 (3H, t, J 7.1 Hz).

APCI-MS m/z: 293.9 [MH+]

b) 9-Chloro-2,3-dihydro[1,4]dioxino[1,3g]quinoline-8-carboxylic acid

Ethyl 9-chloro-2,3-dihydro[1,4]dioxino[2,3g]quinoline-8-carboxylate (1.1 g, 3.7 mmol) was dissolved in a mixture of ethanol (20 ml) and THF (5 ml). Aqueous NaOH (2M, 20 ml) was added. After stirring at ambient temperature for 1 h 45 min the reaction mixture was acidified with 1 M HCl. The organic solvents were evaporated under reduced pressure and the crude product was isolated by centrifugation. After decantation, the precipitate was re-suspended in water centrifuged again. The procedure was repeated twice and the precipitate was finally dried to give the title compound (0.65 g, 65%).

$^1$H NMR (DMSO-d6): δ 13.78 (1H, bs); 8.94 (1H, s); 7.66 (1H, s); 7.51 (1H, s) and 4.45 (4H, s).

c) 9-Chloro-2,3-dihydro[1,4]dioxino[1,3g]quinoline-8-carboxamide

9-Chloro-2,3-dihydro[1,4]dioxino[1,3g]quinoline-8-carboxylic acid (0.61 g) in thionyl chloride (30 ml) was heated at reflux for 3 h and the reaction mixture was then co-evaporated with toluene. The residue was suspended in ice-cold acetone (25 ml) and treated with ice-cold saturated aqueous ammonia (28%, 1.5 ml) in portions at 0° C. The reaction mixture was stirred at 0° C. for 2 min and then filtered. The solid material was washed with water and dried to give slightly impure title compound (435 mg, 71%). From the aqueous filtrate was precipitated additional title compound (91 mg) which was sufficiently pure to be used without further purification.

$^1$H NMR (DMSO-d6): δ 8.64 (1H, s); 8.10 (1H, bs); 7.85 (1H, bs); 7.58 (1H, s); 7.50 (1H, s) and 4.40 (4H, s).

APCI-MS m/z: 265.0 [MH+]

d) 9-(3-Hydroxymethyl-2-methylanilino)-2,3-dihydro[1,4]dioxino[2,3g]quinoline-8-carboxamide A mixture of 9-chloro-2,3-dihydro[1,4]dioxino[1,3g]quinoline-8-carboxamide (0.090 g, 0.34 mmol), 3-amino-2-methylbenzylalcohol (0.058 g, 0.45 mmol) and acetic acid (80 μl) in DMF (1.6 ml) was heated at 100° C. for 3 h. After cooling, the mixture was diluted with water and made alkaline with 1 M NaOH. Methanol was added and the mixture was heated to partially dissolve the gummy precipitate. After cooling the precipitate was collected by filtration, washed with water and dried to give the title compound (98 mg, 75%).

$^1$H NMR (DMSO-d6): δ 10.78 (1H, s); 8.85 (1H, s); 8.27 (1H, bs); 7.61 (1H, bs); 7.26 (1H, s); 7.17 (1H, d, J 7.4 Hz); 7.03 (1H, t, J 7.6 Hz); 6.79 (1H, s); 6.59 (1H, d J 7.9 Hz); 5.17 (1H, t, J 5.2 Hz); 4.57 (2H, d, J 5.2 Hz); 4.31 (2H, s); 4.21 (2H, s) and 2.27 (3H, s).

APCI-MS m/z: 366.1 [MH+]

The title compounds of examples 186–195 were prepared by a method analogous to that described in Example 3.

EXAMPLE 186

4-[(2-Ethylphenyl)amino]-7-methoxy-6-[2-(propylamino)ethoxy]quinoline-3-carboxamide APCI-MS m/z: 423 [MH+]

EXAMPLE 187

6-[(2-Ethylamino)ethoxy]-4-[(2-ethylphenyl)amino]-7-methoxyquinoline-3-carboxamide APCI-MS m/z: 409 [MH+]

EXAMPLE 188

6-[2-(Isopropylamino)ethoxy]-7-methoxy-4-[(3-methoxy-2-methylphenyl)amino]quinoline-3-carboxamide APCI-MS m/z: 439 [MH+]

EXAMPLE 189

6-[2-(Dimethylamino)ethoxy]-4-{[2-ethyl-3-(hydroxymethyl)phenyl]amino}-7-methoxyquinoline-3-carboxamide Bis(trifluoroacetate)

APCI-MS m/z: 667 [MH+]

EXAMPLE 190

6-[3-(Diethylamino)propoxy]-4-{[3-(hydroxymethyl)-2-methylphenyl]amino}-7-methoxyquinoline-3-carboxamide APCI-MS m/z: 467 [MH+]

EXAMPLE 191

4-{[2-Ethyl-3-(hydroxymethyl)phenyl]amino}-7-methoxy-6-[2-(methylamino)ethoxy]quinoline-3-carboxamide APCI-MS m/z: 425 [MH+]

EXAMPLE 192

4-[(2-Ethylphenyl)amino]-7-methoxy-6-[3-(pyridin-4-ylamino)propoxy]quinoline-3-carboxamide Bis (trifluoroacetate)

APCI-MS m/z: 700 [MH+]

EXAMPLE 193

4-[(2-Ethylphenyl)amino]-7-methoxy-6-[3-[(2-amino-2-oxoethyl)amino]propoxy]-quinoline-3-carboxamide APCI-MS m/z: 600 [MH+]

EXAMPLE 194

4-[(2-Ethylphenyl)amino]-7-methoxy-6-[3-(1H-pyrazol-3-ylamino)propoxy]quinoline-3-carboxamide Trifluoroacetate APCI-MS m/z: 575 [MH+]

EXAMPLE 195

4-[(2-Ethylphenyl)amino]-7-methoxy-6-[3-pyridin-2-ylamino)propoxy]quinoline-3-carboxamide Bis (trifluoroacetate)

APCI-MS m/z: 700 [MH+]

The title compound of Example 196 were prepared by a method analogous to that described in Example 12.

EXAMPLE 196

Ethyl 4-[(3-(aminocarbonyl)-4-{[2-ethyl-3-(hydroxymethyl)phenyl]amino}-6-methoxyquinolin-7-yl)oxy]butanoate Trifluoroacetate APCI-MS m/z: 597 [MH+]

The title compounds of examples 197–218 were prepared by a method analogous to that described in Example 23

EXAMPLE 197

7-[3-(Diethylamino)propoxy]-6-methoxy-4-[(2-methoxyphenyl)amino]quinoline-3-carboxamide APCI-MS m/z: 453 [MH+]

EXAMPLE 198

7-[3-(Ethylamino)propoxy]-6-methoxy-4-{[2-(trifluoromethyl)phenyl]amino}quinoline-3-carboxamide APCI-MS m/z: 463 [MH+]

EXAMPLE 199

7-[3-(Ethylamino)propoxy]-4-[(2-ethylphenyl)amino]-6-methoxyquinoline-3-carboxamide APCI-MS m/z: 423 [MH+]

EXAMPLE 200

4-[(2-Ethylphenyl)amino]-7-[3-(isopropylamino)propoxy]-6-methoxyquinoline-3-carboxamide APCI-MS m/z: 437 [MH+]

EXAMPLE 201

7-[3-(Ethylamino)propoxy]-4-{[2-ethyl-3-(hydroxymethyl)phenyl]amino}-6-methoxyquinoline-3-carboxamide APCI-MS m/z: 453 [MH+]

EXAMPLE 202

4-{[2-Ethyl-3-(hydroxymethyl)phenyl]amino}-6-methoxy-7-[3-(propylamino)propoxy]quinoline-3-carboxamide APCI-MS m/z: 467 [MH+]

EXAMPLE 203

7-[3-(Dimethylamino)propoxy]-4-[(2-ethylphenyl)amino]-6-methoxyquinoline-3-carboxamide Bis(trifluoroacetate)

APCI-MS m/z: 651 [MH+]

EXAMPLE 204

4-[(2-Ethylphenyl)amino]-6-methoxy-7-(3-pyrrolidin-1-ylpropoxy)quinoline-3-carboxamide Bis(trifluoroacetate)

APCI-MS m/z: 677 [MH+]

EXAMPLE 205

7-[3-(Diethylamino)propoxy]-4-[(2-ethylphenyl)amino]-6-methoxyquinoline-3-carboxamide Bis(trifluoroacetate)

APCI-MS m/z: 679 [MH+]

EXAMPLE 206

4-[(2-Ethylphenyl)amino]-6-methoxy-7-(3-piperidin-1-ylpropoxy)quinoline-3-carboxamide Bis(trifluoroacetate)

APCI-MS m/z: 691 [MH+]

EXAMPLE 207

7-[3-(Dimethylamino)propoxy]-4-{[2-ethyl-3-(hydroxymethyl)phenyl]amino}-6-methoxyquinoline-3-carboxamide Bis(trifluoroacetate)

APCI-MS m/z: 681 [MH+]

EXAMPLE 208

7-[3-(Diethylamino)propoxy]-4-{[2-ethyl-3-(hydroxymethyl)phenyl]amino}-6-methoxyquinoline-3-carboxamide Bis(trifluoroacetate)

APCI-MS m/z: 709 [MH+]

EXAMPLE 209

7-{3-[(2-Ethoxyethyl)amino]propoxy}-4-[(2-ethylphenyl)amino]-6-methoxyquinoline-3-carboxamide APCI-MS m/z: 467 [MH+]

EXAMPLE 210

4-[(2-Ethylphenyl)amino]-6-methoxy-7-(3-piperidin-1-ylpropoxy)quinoline-3-carboxamide APCI-MS m/z: 463 [MH+]

EXAMPLE 211

4-[(2-Ethylphenyl)amino]-6-methoxy-7-(3-thiomorpholin-4-ylpropoxy)quinoline-3-carboxamide APCI-MS m/z: 481 [MH+]

EXAMPLE 212

4-{[3-Hydroxymethyl)-2-methylphenyl]amino}-6-methoxy-7-(3-pyrrolidin-1-ylpropoxy)quinoline-3-carboxamide APCI-MS m/z: 465 [MH+]

EXAMPLE 213

7-[3-(1,1-Dioxidothiomorpholin-4-yl)propoxy]-4-[(2-ethylphenyl)amino]-6-methoxyquinoline-3-carboxamide APCI-MS m/z: 513 [MH+]

EXAMPLE 214

4-{[2-Ethyl-3-(hydroxymethyl)phenyl]amino}-6-methoxy-7-(3-pyrrolidin-1-ylpropoxy)quinoline-3-carboxamide APCI-MS m/z: 479 [MH+]

EXAMPLE 215

4-{[2-Ethyl-3-(hydroxymethyl)phenyl]amino}-6-methoxy-7-(3-piperidin-1-ylpropoxy)quinoline-3-carboxamide APCI-MS m/z: 493 [MH+]

EXAMPLE 216

4-{[3-(Hydroxymethyl)-2-methylphenyl]amino}-7-[3-(3-hydroxypiperidin-1-yl)propoxy]-6-methoxyquinoline-3-carboxamide APCI-MS m/z: 495 [MH+]

EXAMPLE 217

4-{[2-Ethyl-3-(hydroxymethyl)phenyl]amino}-6-methoxy-7-[3-(1H-1,2,4-triazol-1-yl)propoxy]quinoline-3-carboxamide Bis(trifluoroacetate)

APCI-MS m/z: 705 [MH+]

EXAMPLE 218

7-(3-Azepan-1-ylpropoxy)-4-[(2-ethylphenyl)amino]-6-methoxyquinoline-3-carboxamide APCI-MS m/z: 477 [MH+]

The title compounds of examples 219–222 were prepared by a method analogous to that described in Example 87.

EXAMPLE 219

6,7-Dimethoxy-4-{[2-(methylthio)phenyl]amino}quinoline-3-carboxamide Trifluoroacetate APCI-MS m/z: 484 [MH+]

EXAMPLE 220

6,7-Dimethoxy-4-[(4-methoxy-2-methylphenyl)amino]quinoline-3-carboxamide Trifluoroacetate APCI-MS m/z: 482 [MH+]

EXAMPLE 221

4-{[2-Bromo-3-(hydroxymethyl)phenyl]amino}-6,7-dimethoxyquinoline-3-carboxamide

APCI-MS m/z: 433 [MH+]

EXAMPLE 222

4-{[2-Ethyl-3-(hydroxymethyl)phenyl]amino}-6,7-dimethoxyquinoline-3-carboxamide

APCI-MS m/z: 382 [MH+]

Syntheses of Anilines Used Above

Methyl 2-methyl-3-nitrobenzyl ether

To a solution of sodium (0.10 g, 4.3 mmol) in methanol (40 ml) was added 2-methyl-3-nitrobenzylchloride (0.50 g, 2.7 mmol) and catalytic amounts of LiI under nitrogen. After the reaction occurred at 40° C. over night, the solvent evaporated and the residue was purified by chromatography (heptane/EtOAc) to give the title compound 450 mg, (92%) as a yellow oil.

¹H NMR (CDCl₃): δ 7.70 (1H, d); 7.58 (1H, d); 7.29 (1H, t); 4.49 (2H, s); 3.43 (3H, s); 2.42 (3H, s).

Isobutyl 2-methyl-3-nitrobenzyl ether

The same procedure as in methyl 2-methyl-3-nitrobenzyl ether was used, to give the title compound 486 mg, (81%) as a yellow oil.

¹H NMR (CDCl₃): δ 7.71 (1H, d); 7.58 (1H, d); 7.29 (1H, t); 4.52 (2H, s); 3.27 (2H, d); 2.42 (3H, s); 1.91 (1H, m); 0.93 (6H, d).

3-(Methoxymethyl)-2-methylaniline

A mixture of methyl 2-methyl-3-nitrobenzyl ether (0.19 g, 1.05 mmol), and 5% Pd/C (70 mg) in EtOAc/EtOH 1:1 (14 ml) was hydrogenated at 1 atm over night. The mixture was filtered through Celite, and the filtrate was concentrated to give the title compound 125 mg (78%) as a yellow oil.

¹H NMR (CDCl₃): δ 6.99 (1H, t); 6.75 (1H, d); 6.66 (1H, d); 4.42 (2H, s); 3.60 (2H, br s); 3.37 (3H, s); 2.12 (3H, s)

3-(Isobutoxymethyl)-2-methylaniline

The title compound was prepared by the same procedure as in 3-(methoxymethyl)-2-methylaniline.

¹H NMR (CDCl₃): δ 6.99 (1H, t); 6.76 (1H, d); 6.65 (1H, d); 4.46 (2H, s); 3.60 (2H, br s); 3.21 (2H, d); 2.13 (3H, s); 1.89 (1H, m); 0.91 (6H, d).

2-(3-Amino-2-methylphenyl)acetonitrile 2-(2-Methyl-3-nitrophenyl)acetonitrile (Askam, V. et al. J. Chem. Soc. C (1969)1935–1936;) was hydrogenated over 5% palladium-charcoal 50 mg in EtOAc/EtOH 1:1 (14 ml) for three hours. The mixture was filtered through celite, and the filtrate was concentrated to give the title compound 77 mg (77%) as a white powder.

¹H NMR (CDCl₃): δ 7.03 (1H, t); 6.78 (1H, d); 6.68 (1H, d); 3.66 (2H, br s); 3.63 (2H, s); 2.22 (3H, s).

N-(2-methyl-3-nitrobenzyl)-1-ethanamine

A mixture of 2-methyl-3-nitrobenzylchloride (0.50 g, 2.7 mmol) and ethylamine (2.76 g, 61.2 mmol) in THF (10 ml)/MeOH (5 ml) was stirred at ambiend temperature for 48 h. The solvent was reduced and the recidue was dissolved in EtOAc/aq. K₂CO₃ solution. The aqueous phase was extracted with EtOAc (×2). The combined organic layers were washed with brine, dried (Na₂SO₄), and concentrated to give the title compound 0.46 g (86%) as a yellow oil.

¹H NMR (CDCl₃): δ 7.65 (1H, d); 7.55 (1H, d); 7.27 (1H, d); 3.83 (2H, s); 2.72 (2H, q); 2.45 (3H, s); 1.15 (3H, t).

3-[(Ethylamino)methyl]-2-methylaniline

N-(2-methyl-3-nitrobenzyl)-1-ethanamine (0.46 g, 2.3 mmol) was hydrogenated over 5% palladium-charcoal 80 mg in EtOAc/EtOH 1:1 (14 ml) for four hours. The mixture was filtered through celite, and the filtrate was concentrated to give the title compound 0.373 g (97%) as a pale yellow oil.

¹H NMR (CDCl₃): δ 6.98 (1H, t); 6.74 (1H, d); 6.62 (1H, d); 3.74 (2H, s); 3.60 (2H , br s); 2.71 (2H, q); 2.14 (3H, s); 1.13 (3H, t).

tert-Butyl 3-amino-2-methylbenzyl(ethyl)carbamate

To a solution of 3-[(ethylamino)methyl]-2-methylaniline (0.32 g, 1.95 mmol) in THF (20 ml), was added di-tert-butyl dicarbonate 0.43 g (1.97 mmol). After 16 h stirring at ambient temperature, the solvent evaporated, and the residue was purified by chromatography to give the title compound 0.51 g (99%) as a colourless oil.

¹H NMR (CDCl₃): δ 6.97 (1H, s); 6.61 (2H, m); 4.42 (2H, br s); 3.60 (2H, br s); 3.12 (2H, br d); 2.08 (3H, s); 1.45 (9H, br s); 0.98 (3H, br s).

tert-Butyl 2-aminobenzylcarbamate

To ice cooled solution of 2-amino-benzylamine (1.2 g, 10 mmol) in THF (70 ml) was added di-tert-butyl dicarbonate (2.15 g, 9.9 mmol). After 18 h stirring at ambient temperature, the solvent was reduced and the precipitate was collected by filtration, washed with cold ether (×2), heptane (×2) and dried, to give the title compound 1.9 g (85%) as a pale yellow powder.

¹H NMR (CDCl₃): δ 7.09 (1H, m); 7.02 (1H, m); 6.66 (1H, m); 4.76 (1H, br s); 4.25 (2H, d); 4.21 (2H, br s); 1.43 (9H, s)

2-(3-Amino-2-methylphenyl)-N-ethylacetamide

A mixture of 2-(3-amino-2-methylphenyl)acetic acid (0.32 g, 1.78 mmol) and thionyl chloride (2 ml) was refluxed for 1.5 hour. After cooling the excess thionyl chloride was removed by evaporation. Last traces of thionyl chloride were removed by azeotroping with toluene.

The residue dissolved in dry EtOAc (2 ml) and cooled in an ice-bath. Ethylamine (2 ml) was added and the reaction occurred over night at ambient temperature. The organic layer was washed with water, brine, dried over Na₂SO₄ and evaporated to give an white powder, which was hydrogenated on 5% palladium-charcoal (70 mg) in EtOAc/EtOH 1:1 25 ml for 3 hours. The mixture was filtered through celite, and the filtrate was concentrated to give an oil which was further purified by chromatography on silica, (CH₂Cl₂/MeOH), to give 0.266 g (78%) of the title compound as a white solid.

¹H NMR (CDCl₃): δ 6.99 (1H, t); 6.65 (1H, d); 6.61 (1H, d); 5.32 (1H, br s); 3.66 (2H, br s); 3.55 (2H, s); 3.20 (2H, m); 2.41 (3H, s); 1.05 (3H, t).

2-(3-amino-2-methylphenyl)-N-(2-hydroxyethyl)acetamide

A mixture of 2-(3-amino-2-methylphenyl)acetic acid (0.33 g, 1.84 mmol) and thionyl chloride (2 ml) was refluxed for 1.5 hour. After cooling the excess thionyl chloride was removed by evaporation. Last traces of thionyl chloride were removed by azeotroping with toluene.

The residue dissolved in dry EtOAc (2 ml) and cooled in an ice-bath. 2-Aminoethanol (2 ml) was added and the reaction occurred over night at ambient temperature. The organic layer was diluted with EtOAc (15 ml), washed with water, brine, dried over Na₂SO₄ and evaporated to give an white powder, which was hydrogenated on 5% palladium-charcoal (70 mg) in ethanol (20 ml) overnight. The mixture was filtered through celite, and the filtrate was concentrated to give 0.28 (73%) of the title compound as a white solid.

¹H NMR (DMSO-d₆): δ 7.69 (1H, m); 6.77 (1H, t); 6.49 (1H, d); 6.39 (1H, d); 4.70 (2H, br s); 4.62 (1H, t); 3.36 (2H, q); 3.34 (3H, s); 3.09 (2H, q) 1.93 (3H, s).

APCI-MS m/z: 209.2 [MH+]

3-(Aminomethyl)-2-methylaniline

A mixture of 2-methyl-3-nitrobenzylchloride (0.70 g, 3.77 mmol), sodium azid (1 g, 15.4 mmol), ethanol (10 ml) and water (2 ml) was heated at 45° C. over night. The mixture was filtered, the filtrate was concentrated, and the residue was purified by chromatography on silica (heptane/EtOAc) to give the compound 2-methyl-3-nitrobenzylazide 0.35 g, which was hydrogenated over 5% palladium-charcoal 80 mg in EtOAc/EtOH 1:1 (14 ml), over night. The mixture was filtered through Celite, and the filtrated was concentrated to give 0.23 g (45%) of the title compound as a white solid.

¹H NMR (DMSO-d₆): δ (1H, t); 6.52 (2H, t); 4.67 (2H, br s); 3.59 (2H, s); 1.96 (3H, s).

tert-Butyl 3-amino-2-methylbenzylcarbamate

To a solution of 3-[(ethylamino)methyl]-2-methylaniline (0.21 g, 1.54 mmol) in THF (20 ml), was added di-tert-butyl dicarbonate (0.35 g, 1.97 mmol). After 18 h stirring at ambiend temperature, the solvent evaporated, and the residue was purified by chromatography on silica (CH₂Cl₂/MeOH) to give 0.51 g (99%) of the title compound as a colourless oil.

¹H NMR (CDCl₃): δ 6.99 (1H, t); 6.69 (1H, d); 6.64 (1H, d); 4.63 (1H, br s); 4.29 (2H, d); 3.63 (2H, br s); 2.10 (3H, s); 1.45 (9H, s).

3-(2-Nitrophenyl)propanoic acid

The title compound was prepared by a modification of the procedure reported by Grob et al. Helv. Chim. Acta 206 (1961)1736–1747.

Sodium hydride (60% in paraffin oil, 1.0 g, 25 mmol) was added to a solution of diethyl malonate (3.2 g, 20 mmol) in DMF (20 ml) and the mixture was stirred for 3 min. 1-Bromomethyl-2-nitrobenzene (4.3 g, 20 mmol) was then added in portions during 5 min. The reaction mixture was stirred for 3 h, diluted with water, and extracted twice with ethyl acetate. The combined organic phases was washed with water and evaporated. The residue was suspended in acetic acid (40 ml) and 7.5 M HCl (10 ml) was added. The mixture was refluxed for 19 h, cooled and partitioned between diethyl ether and saturated aqueous NaHCO₃. The organic phase was washed with saturated aqueous NaHCO₃ and then acidified with 2M HCl. The precipitate was collected by filtration and dried to give the title compound (2.22 g, 77%).

¹H NMR (CDCl₃): δ 7.97 (1H, dd, J 8.1 and 1.3 Hz); 7.57 (1H, dt, J 7.5 and 1.3 Hz); 7.47–7.37 (2H, m); 3.24 (2H, t, J 7.6 Hz); and 2.81 (2H, t, J 7.6 Hz).

4Nitro-1-indanone

The title compound was prepared essentially as described by Grob et al. Helv. Chim. Acta 206(1961)1736–1747.

3-(2-Nitrophenyl)propanoic acid (2.17 g, 11.1 mmol) in thionyl chloride (30 ml) was heated at reflux temperature for 1.5 h and the reaction mixture was then evaporated. The residue was dissolved in carbon disulfide (15 ml, distilled over AlCl₃) and AlCl₃ (3.2 g, 24 mmol) was added with stirring. The mixture was heated at reflux temperature for 4 h and the solvent was then evaporated using a stream of nitrogen at ambient temperature. To the residue was added with stirring a mixture of concentrated H₂SO₄ (5.3 ml) and ice (33 g) followed by toluene (25 ml). The mixture was stirred until all solid material was dissolved and the organic phase was then separated. The water phase was extracted twice with diethyl ether and the combined organic phases were washed subsequently with saturated NaHCO₃, water and brine and finally dried over MgSO₄ filtered and evaporated. The residue was chromatographed on a column of silica (2×18 cm) using ethyl acetate-heptane (1:3) as eluent to give the title compound (0.8 g, 40%).

¹H NMR (CDCl₃): δ 8.49 (1H, dd, J 8.0 and 1.1 Hz); 8.10 (1H, d, J 7.5 Hz, further coupled); 7.63 (1H, t, J 7.8 Hz, further coupled); 3.67 (2H, m) and 2.82 (2H, m).

4-Amino-1-indanone

4-Nitro-1-indanone (0.84 g, 4.75 mmol) was suspended in aqueous hydrochloric acid (9 M, 40 ml) and stannous chloride (3 g, 15.8 mmol) was added. The mixture was stirred at ambient temperature. After 2 h a clear solution was obtained. The stirring was continued for 23 h after which time a yellow precipitate had formed. The reaction mixture was diluted with water and washed trice with methylene chloride. The aqueous phase was made alkaline with 2 M aqueous NaOH and extracted four times with methylene chloride. The combined organic phases was washed with water, dried (Na₂SO₄), filtered, evaporated and finally dried to give the title compound (630 mg, 90%).

¹H NMR (CDCl₃): δ 7.28–7.18 (2H, m); 6.93 (1H, d, J 7.0 Hz); 2.92 (2H, t, J 5.6 Hz, further coupled) and 2.71 (2H, t, J 5.5 Hz, further coupled).

2-Bromo-3-aminobenzyl alcohol

The compound is reported in (Cladingboel, David E. et al. J. Chem. Soc. Chem. Commun.; EN; 21; 1990;1543–1544.)

Methyl 3-nitro-2-vinylbenzoate

The compound is reported in (Söderberg, Björn C. et al. J. Org. Chem. 1997; 62; 5838–5845), Methyl 3-amino-2-ethylbenzoate A mixture of methyl 3-nitro-2-vinylbenzoate (1.1 g, 5.31 mmol), and 5% Pd/C (100 mg) in EtOAc/EtOH 1:1 (50 ml) was hydrogenated at 3 atm over night. The mixture was filtered through Celite, and the filtrate was concentrated to give the title compound 0.93 g (97%) as a colourless oil.

¹H NMR (CDCl₃): d 7.20 (1H, q); 7.05 (1H, t); 6.82 (1H, q); 3.88 (3H, s); 3.75 (2H, br s); 2.78 (2H, q); 1.24 (3H, t).

(3-Amino-2-ethylphenyl)methanol

To a solution of methyl 3-amino-2-ethylbenzoate (0.83 g, 4.63 mmol), in THF (40 ml) was added Lithium aluminium hydride (0.9 g, 23.7 mmol). The mixture was heated at 50 C. for 5 h, cooled to 0 C. and hydrolysed cautiously with water. The slurry was extracted with EtOAc (×5). The extracts were washed with brine, dried Na₂SO₄, and evaporated. The residue was purified by chromatography (CH₂Cl₂/MeOH) to give the title compound 0.63 g (89%) as a white powder.

¹H NMR (CDCl₃): δ 7.05 (1H, t); 6.82 (1H, d); 6.70 (1H, d); 4.68 (2H, d); 3.71 (2H, br s); 2.68 (2H, q); 1.47 (1H, t); 1.23 (3H, t).

Pharmacological Data

JAK3 HTRF assay

The JAK3 kinase assay utilizes a fusion protein (Jak3 kinase domain fused to Glutathione S-transferase, GST) coexpressed in E. Coli with GroEL/S, and purified by affinity chromatography on Glutathione Sepharose. The enzyme is diluted in 10 mM Tris-HCl, 150 mM NaCl, 5% mannitol, 2 mM 2-mercaptoethanol and 30% glycerol. The substrate in the kinase reaction is a biotinylated peptide of the autophosphorylation site of JAK3 (biotin-LPDKDYYV-VREPG) used at 2 μM. Assay conditions are as follows: JAK3, compound and substrate was incubated in 25 mM Trizma base, 5 mM MgCl₂, 5 mM MnCl₂, 0.05% TritonX-100 and 2 μM ATP for 45 min at RT. Reaction volume is 20 μM. Stopsolution is added for a final concentration of 100 μM EDTA. Finally 0.065 mg/ml PT66-K and 10.42 μM SA-XL665 are added in 50 mM Hepes, 0.5 M KF and 0.1% BSA. The plate is read in a Discovery instrument after 60 min incubation.

The compounds of the examples have an IC50 less than 25 μM

What is claimed is:

1. A compound of formula (IA):

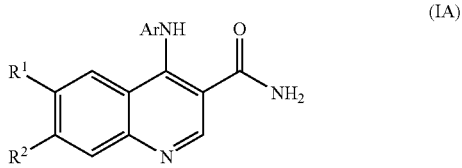

in which
Ar is phenyl substituted by ethyl, propyl, hydroxymethyl or CO$_2$H or disubstituted by methyl and hydroxymethyl;
R$^1$ is methoxy, ethoxy or a group OCH$_2$CONH$_2$, OCH$_2$CH$_2$OCH$_3$, or O(CH$_2$)$_p$NR$^4$R$^5$ where p is 2 or 3 and R$^4$ and R$^5$ are hydrogen, methyl, ethyl or propyl or together R$^4$ and R$^5$ form a pyrrolidine, imidazole or morpholine ring;
R$^2$ is methoxy, ethoxy or O(CH$_2$)$_p$NR$^4$R$^5$ where p is 2, 3 or 4 and R$^4$ and R$^5$ are hydrogen, methyl or ethyl or one of R$^4$ or R$^5$ is methyl and the other is pyridyl or pyrazole or R$^4$ and R$^5$ form a piperidine, hydroxypiperidine, thiomorpholine, morpholine, pyrrolidine, 2,6-dimethylmorpholine imidazole or triazole ring,
or a pharmaceutically acceptable salt or solvate thereof, provided that when A is phenyl substituted by ethyl or propyl or disubstituted by methyl, then R$^1$ and R$^2$ are not both methoxy, R$^1$ and R$^2$ are not both ethoxy or one of R$^1$/R$^2$ is not methoxy when the other is ethoxy.

2. A compound of claim 1 selected from:
4-(2-ethylanilino)-6-methoxy-7-{2-[methyl(4-pyridinyl)amino]ethoxy}-3-quinolinecarboxamide,
4-[3-(hydroxymethyl)-2-methylanilino]-6-methoxy-7-[3-(4-thiomorpholinyl)propoxy]-3-quinolinecarboxamide,
4-[3-(hydroxymethyl)-2-methylanilino]-6-methoxy-7-[3-(1-piperidinyl)propoxy]-3-quinolinecarboxamide,
4-[3-(hydroxymethyl)-2-methylanilino]-6-methoxy-7-[3-(4-morpholinyl)propoxy]-3-quinolinecarboxamide,
7-[3-(dimethylamino)propoxy]-4-(2-ethylanilino)-6-methoxy-3-quinolinecarboxamide,
7-[3-(dimethylamino)propoxy]-4-[3-(hydroxymethyl)-2-methylanilino]-6-methoxy-3-quinolinecarboxamide,
7-{3-[(2R,6S)-2,6-dimethylmorpholinyl]propoxy}-4-[3-(hydroxymethyl)-2-methylanilino]-6-methoxy-3-quinolinecarboxamide,
4-(2-ethylanilino)-6-methoxy-7-[3-(4-morpholinyl)propoxy]-3-quinolinecarboxamide,
4-(2-ethylanilino)-6-methoxy-7-[4-(4-morpholinyl)butoxy]-3-quinolinecarboxamide,
4-(2-ethylanilino)-6-methoxy-7-{3-[methyl(4-pyridinyl)amino]propoxy}-3-quinolinecarboxamide,
4-(2-ethylanilino)-7-methoxy-6-[2-(methylamino)ethoxy]-3-quinolinecarboxamide,
7-{3-[(2S,6S)-2,6-dimethylmorpholinyl]propoxy}-4-[3-(hydroxymethyl)-2-methylanilino]-6-methoxy-3-quinolinecarboxamide,
4-(2-ethylanilino)-7-[3-(1H-imidazol-1-yl)propoxy]-6-methoxy-3-quinolinecarboxamide,
6-(2-aminoethoxy)-4-(2-ethylanilino)-7-methoxy-3-quinolinecarboxamide,
6-methoxy-4-[2-(methylsulfanyl)anilino]-7-[3-(4-morpholinyl)propoxy]-3-quinolinecarboxamide,
6-methoxy-7-[3-(4-morpholinyl)propoxy]-4-(2-toluidino)-3-quinolinecarboxamide,
4-(2-ethylanilino)-6-methoxy-7-[3-(1H-1,2,4-triazol-1-yl)propoxy]-3-quinolinecarboxamide,
4-(2-ethylanilino)-6-methoxy-7-[2-(methylamino)ethoxy]-3-quinolinecarboxamide,
4-(2-ethylanilino)-6-methoxy-7-(2-methoxyethoxy)-3-quinolinecarboxamide,
4-(2-ethylanilino)-7-(3-hydroxypropoxy-6-methoxy-3-quinolinecarboxamide,
6-methoxy-7-[2-(4-morpholinyl)ethoxy]-4-(2-toluidino)-3-quinolinecarboxamide,
4-[3-(hydroxymethyl)-2-methylanilino]-7-methoxy-6-[2-(1-pyrrolidinyl)ethoxy]-3-quinolinecarboxamide,
3-{[3-(aminocarbonyl)-6,7-dimethoxy-4-quinolinyl]amino}-2-methylbenzoic acid,
4-[3-(hydroxymethyl)-2-methylanilino]-6,7-dimethoxy-3-quinolinecarboxamide,
4-(2-ethylanilino)-7-[2-(1H-imidazol-1-yl)ethoxy]-6-methoxy-3-quinolinecarboxamide,
4-[3-(2-hydroxyethyl)-2-methylanilino]-6,7-dimethoxy-3-quinolinecarboxamide,
7-methoxy-6-{[2-(4-morpholinyl)ethyl]amino}-4-(2-toluidino)-3-quinolinecarboxamide,
4-(2-ethylanilino)-6-[3-(1H-imidazol-1-yl)propoxy]-7-methoxy-3-quinolinecarboxamide,
4-(2-ethylanilino)-7-methoxy-6-[2-(1-pyrrolidinyl)ethoxy]-3-quinolinecarboxamide,
7-(3-aminopropoxy)-4-(2-ethylanilino)-6-methoxy-3-quinolinecarboxamide,
methyl 4-{[3-(aminocarbonyl)-6-methoxy-4-(2-toluidino)-7-quinolinyl]oxy}butanoate,
4-[3-(aminomethyl)-2-methylanilino]-6,7-dimethoxy-3-quinolinecarboxamide,
6-{[3-(1H-imidazol-1-yl)propyl]amino}-7-methoxy-4-(2-toluidino)-3-quinolinecarboxamide,
4-[3-(hydroxymethyl)-2-methylanilino]-7-methoxy-6-(2-methoxyethoxy)-3-quinolinecarboxamide,
6-[2-(dimethylamino)ethoxy]-4-(2-ethylanilino)-7-methoxy-3-quinolinecarboxamide,
4-[3-(cyanomethyl)-2-methylanilino]-6,7-dimethoxy-3-quinolinecarboxamide,
4-[3-(2-amino-2-oxoethyl)-2-methylanilino]-6,7-dimethoxy-3-quinolinecarboxamide,
6-(3-aminopropoxy)-4-(2-ethylanilino)-7-methoxy-3-quinolinecarboxamide,
4-[3-(hydroxymethyl)-2-methylanilino]-7-methoxy-6-[3-(4-morpholinyl)propoxy]-3-quinolinecarboxamide,
4-[3-(hydroxymethyl)-2-methylanilino]-7-methoxy-6-[2-(4-morpholinyl)ethoxy]-3-quinolinecarboxamide,
and pharmaceutically acceptable salts thereof.

3. A compound of claim 1 selected from:
4-[(2-ethylphenyl)amino]-7-methoxy-6-[3-(pyridin-4-ylamino)propoxy]quinoline-3-carboxamide,
4-[(2-ethylphenyl)amino]-7-methoxy-6-[3-[(2-amino-2-oxoethyl)amino]propoxy]-quinoline-3-carboxamide,
4-[(2-ethylphenyl)amino]-7-methoxy-6-[3-(1H-pyrazol-3-ylamino)propoxy]quinoline-3-carboxamide,
4-[(2-ethylphenyl)amino]-7-methoxy-6-[3-(pyridin-2-ylamino)propoxy]quinoline-3-carboxamide,
Ethyl 4-[(3-(aminocarbonyl)-4-{[2-ethyl-3-(hydroxymethyl)phenyl]amino}-6-methoxyquinolin-7-yl)oxy]butanoate,
7-[3-(diethylamino)propoxy]-6-methoxy-4-[(2-methoxyphenyl)amino]quinoline-3-carboxamide, 7-[3-(ethylamino)propoxy]-6-methoxy-4-{[2-(trifluoromethyl)phenyl]amino}quinoline-3-carboxamide, 7-[3-(ethylamino)propoxy]-4-[(2-ethylphenyl)amino]-6-methoxyquinoline-3-carboxamide, 4-[(2-ethylphenyl)amino]-7-[3-(isopropylamino)propoxy]-6-methoxyquinoline-3-carboxamide, 7-[3-(ethylamino)propoxy]-4-{[2-ethyl-3-(hydroxymethyl)phenyl]amino}-6-methoxyquinoline-3-carboxamide, 4-{[2-ethyl-3-(hydroxymethyl)phenyl]amino}-6-methoxy-7-[3-(propylamino)propoxy]quinoline-3-carboxamide, 7-[3-(dimethylamino)propoxy]-4-[(2-ethylphenyl)amino]-6-methoxyquinoline-3-carboxamide, 4-[(2-ethylphenyl)amino]-6-methoxy-7-(3-pyrrolidin-1-ylpropoxy)quinoline-3-carboxamide, 7-[3-(diethylamino)propoxy]-4-[(2-ethylphenyl)amino]-6-methoxyquinoline-3-carboxamide, 4-[(2-ethylphenyl)amino]-6-methoxy-7-(3-piperidin-1-ylpropoxy)quinoline-3-carboxamide, 7-[3-(dimethylamino)propoxy]-4-{[2-ethyl-3-(hydroxymethyl)phenyl]amino}-6-methoxyquinoline-3-carboxamide, 7-[3-(diethylamino)propoxy]-4-{[2-ethyl-3-(hydroxymethyl)phenyl]amino}-6-methoxyquinoline-3-carboxamide, 7-{3-[(2-ethoxyethyl)amino]propoxy}-4-[(2-ethylphenyl)amino]-6-methoxyquinoline-3-carboxamide, 4-[(2-ethylphenyl)amino]-6-methoxy-7-(3-piperidin-1-ylpropoxy)quinoline-3-carboxamide, 4-[(2-ethylphenyl)amino]-6-methoxy-7-(3-thiomorpholin-4-ylpropoxy)quinoline-3-carboxamide, 4-{[3-(hydroxymethyl)-2-methylphenyl]amino}-6-methoxy-7-(3-pyrrolidin-1-ylpropoxy)quinoline-3-carboxamide, 4-{[2-ethyl-3-(hydroxymethyl)phenyl]amino}-6-methoxy-7-(3-pyrrolidin-1-ylpropoxy)quinoline-3-carboxamide, 4-{[2-ethyl-3-(hydroxymethyl)phenyl]amino}-6-methoxy-7-(3-piperidin-1-ylpropoxy)quinoline-3-carboxamide, 4-{[3-(hydroxymethyl)-2-methylphenyl]amino}-7-[3-(3-hydroxypiperidin-1-yl)propoxy]-6-methoxyquinoline-3-carboxamide, 4-{[2-ethyl-3-(hydroxymethyl)phenyl]amino}-6-methoxy-7-[3-(1H-1,2,4-triazol-1-yl)propoxy]quinoline-3-carboxamide, and pharmaceutically acceptable salts thereof.

4. A pharmaceutical composition comprising a compound of claim 1 or a pharmaceutically acceptable salt thereof in association with a pharmaceutically acceptable carrier.

5. A method of treating a disease or condition mediated by JAK3 wherein the disease or condition is asthma, host versus graft rejection/transplantation or rheumatoid arthritis, the method comprising administering to a patient in need of such treatment a compound of claim 1 or a pharmaceutically acceptable salt thereof.

6. A process for the preparation of a compound of formula I(a) as claimed in claim 1 which comprises:

(a) reaction of a compound of formula (II):

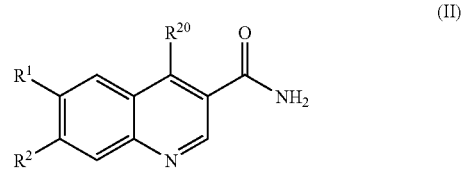

(II)

in which $R^1$ and $R^2$ are as defined in formula (Ia) or are protected derivatives thereof and $R^{20}$ is a leaving group, with a compound of formula (III):

Ar(CR$_2$)$_2$—NH$_2$ (III)

in which Ar and R are as defined in formula (I) or are protected derivatives thereof, followed as needed by removing any protecting groups converting a compound of formula (Ia) into a further compound of formula (Ia) by forming a pharmaceutically acceptable salt.

7. A process for the preparation of a compound of claim 1, comprising:

(a) reaction of a compound of formula (IIa):

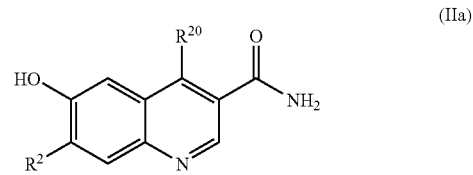

(IIa)

with a group L—CH$_2$CONH$_2$, L—CH$_2$CH$_2$OCH$_3$, or L—(CH$^2$)$_p$NR$^4$R$^5$ wherein L is a leaving group and p is 2 or 3 and $R^4$ and $R^5$ are hydrogen, methyl, ethyl or propyl or together $R^4$ and $R^5$ form a pyrrolidine, imidazole or morpholine ring, followed as needed by removing any protecting groups converting a compound of formula (Ia) into a further compound of formula (Ia) by forming a pharmaceutically acceptable salt; or (b) reaction of a compound of formula (IIba):

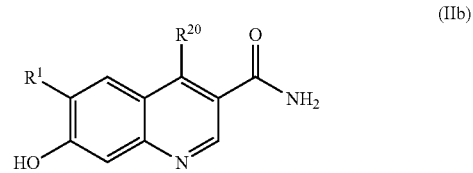

(IIb)

with a group L—(CH$_2$)$_n$NR$^4$R$^5$ wherein L is a leaving group and O(CH$_2$)$_p$NR$^4$R$^5$, p is 2, 3 or 4 and $R^4$ and $R^6$ are hydrogen, methyl or ethyl or one or $R^4$ or $R^5$ is methyl and the other is pyridyl or pyrazole or $R^4$ and $R^5$ form a piperidine, hydroxypiperidine, thiomorpholine, morpholine, pyrrolidine, 2,6-dimethylmorpholine imidazole or triazole ring followed as needed by removing any protecting groups converting a compound of formula (Ia) into a further compound of formula (Ia) by forming a pharmaceutically acceptable salt.

* * * * *